US005665890A

United States Patent [19]
Jacobsen et al.

[11] Patent Number: 5,665,890
[45] Date of Patent: Sep. 9, 1997

[54] STEREOSELECTIVE RING OPENING REACTIONS

[75] Inventors: Eric N. Jacobsen, Boston; James L. Leighton, Sommerville; Luis E. Martinez, Cambridge, all of Mass.

[73] Assignee: President and Fellows of Harvard College, Cambridge, Mass.

[21] Appl. No.: 403,374

[22] Filed: Mar. 14, 1995

[51] Int. Cl.$^6$ .......................... C07B 53/00; C07B 57/00; C07C 247/00; C07D 317/36
[52] U.S. Cl. ............................................. 549/230; 502/158
[58] Field of Search ............................ 502/158; 549/230

[56] References Cited

U.S. PATENT DOCUMENTS

| | | | |
|---|---|---|---|
| 3,868,401 | 2/1975 | Aratani et al. | 260/468 |
| 4,151,195 | 4/1979 | Warnant et al. | 260/465 |
| 4,471,130 | 9/1984 | Katsuki et al. | 549/523 |
| 4,538,003 | 8/1985 | Tam | 568/656 |
| 4,565,845 | 1/1986 | Inoue et al. | 525/25 |
| 4,594,439 | 6/1986 | Katsuki et al. | 549/523 |
| 4,663,467 | 5/1987 | Kruper, Jr. et al. | 549/229 |
| 4,822,899 | 4/1989 | Groves et al. | 549/533 |
| 4,870,208 | 9/1989 | Chan et al. | 562/579 |
| 4,885,376 | 12/1989 | Verkade | 556/18 |
| 4,965,364 | 10/1990 | Marko et al. | 546/134 |
| 5,093,491 | 3/1992 | Ellis, Jr. et al. | 540/135 |
| 5,126,494 | 6/1992 | Gilheany et al. | 568/807 |
| 5,250,731 | 10/1993 | Burk | 564/150 |
| 5,254,704 | 10/1993 | Takano et al. | 549/552 |
| 5,258,553 | 11/1993 | Burk | 568/12 |
| 5,296,595 | 3/1994 | Dolye | 540/200 |
| 5,310,956 | 5/1994 | Takano et al. | 549/529 |
| 5,312,957 | 5/1994 | Casalnuovo et al. | 558/410 |
| 5,321,143 | 6/1994 | Sharpless et al. | 549/34 |
| 5,352,814 | 10/1994 | Katsuki et al. | 556/50 |
| 5,360,938 | 11/1994 | Babin et al. | 568/449 |

FOREIGN PATENT DOCUMENTS

| | | |
|---|---|---|
| 0 342 615 | 11/1989 | European Pat. Off. |
| WO91/14694 | 10/1991 | WIPO |
| WO93/03838 | 3/1993 | WIPO |

OTHER PUBLICATIONS

Maruyama, K. et al. (1991) "Cobalt Schiff Base Complex Catalysed Solvolytic Ring Opening of Epoxy Compounds" *React. Kinet. Catal. Lett.*, vol. 45, No. 2, pp. 165–171.

Martinez, L. et al. (1995) "Highly Enantioselective Ring Opening of Epoxides Catalyzed by (salen)Cr(III) Complexes" *J. Am. Chem. Soc.*, vol. 117, pp. 5897–5898.

Leighton, J. et al (1996) "Efficient Synthesis of (R)-4-((Trimethylsilyl)oxy)-2-cyclopentenone by Enantioselective Catalytic Epoxide Ring Opening" *Journal of Organic Chemistry*, vol. 61, No. 1, pp. 389–390.

Hayashi, M. et al. (1994) "Novel Asymmetric Ring-opening Reactions of Symmetrical N-Acylaziridines with Arenethiols Catalysed by Chiral Dialkyl Tartrate–Diethylzinc Complexes" *J. Chem. Soc., Chem. Commun.* No. 23, pp. 2699–2700.

Hayashi, M. et al. (1991) "Asymmetric Ring Opening of Symmetrical Epoxides with Trimethylsilyl Azide Using Chiral Titanium Complexes" *Synlett*, No. 11 pp. 774–776.

Adolfsson, H. et al. (1995) "Chiral Lewis Acid Catalysed Asymmetric Nucleophilic Ring Opening of Cyclohexene Oxide" *Tetrahedron: Asymmetry*, vol. 6, No. 8, pp. 2023–2031.

Adam, W. et al. (1994) "Tridentate β-Hydroperoxy Alcohols As Novel Oxygen Donors For The Titanium–Catalyzed Epoxidation of v,δ-Unsaturated α,β-Diols: A Direct Diastereoselective Synthesis Of Epoxy Diols" *Angew. Chem. Int. Ed. Engl.* 33(10): 1170–1108.

Agarwal, D. et al. (1992) "Olefin Epoxidation Using Iron (III) Schiff Base Complexes As Catalyst" *Indian Journal of Chemistry* 31A:785–787.

Barili, P et al. (1993) "Regio–and Stereochemistry Of The Acid Catalyzed And Of A Highly Enantioselective Enzymatic Hydrolysis of some Epoxyterahydrofurans" *Tetrahedron* 49(28):6263–6276.

Brandes, B. and E. Jacobsen (1994) "Highly Enantioselective, Catalytic Epoxidation Of Trisubstituted Olefins" *J. of Am. Chem. Soc.* 59:4378–80.

Chang, S. et al. (1994) "Effect of Chiral Quaternary Ammonium Salts On (Salen) Mn–Catalyzed Epoxidation Of Cis–Olefins. A Highly Enantioselective, Catalytic Route to Trans–Epoxides" *J. Am. Chem. Soc.* 116:(15):6937–8.

Chen, X. et al. (1993) "Microbiological Transformations. 27. The First Examples for Preparative–Scale Enantioselective or Diastereoselective Epoxide Hydrolyses Using Microorganisms. An Unequivocal Access to All Four Bisabolol Stereoisomers" *J. Am. Chem. Soc.* 58(20):5528–32.

Collman, J. et al. (1993) "Regioselective and Enantioselective Epoxidation Catalyzed By Metalloporphyrins" *Science* 261:1404–1411.

Colloman, J. et al. (1993) "Enantioselective Epoxidation Of Unfunctionalized Olefins Catalyzed By Threitol–Strapped Manganese Prophyrins" *J. Am. Chem. Soc.* 115:3834–3835.

Corey, E. and F. Hannon (1987) "Chiral Catalysts For The Enantioselective Addition Of Organometallic Reagents To Aldehydes" *Tetrahedron Letters* 28(44)5233–5236.

Desimoni, G. et al. (1992) "Copper(II) In Organic Synthesis. X (*). The Importance of Steric Hindrance In The Design of Chiral Tridentate Ligand Copper (II) Catalysts For Enantiosective Michael Reactions(**)" *Gazzeta Chimica Italiana* 122:268–273.

Emziane, M. et al. ( 1988) "Asymmetric Ring–Opening Of Cyclohexene Oxide With Trimethylsiyl Azide In The Presence Of Titanium Isopropoxide/Chiral Ligand" *J. of Organometallic Chemistry* 346:C7–C10.

(List continued on next page.)

*Primary Examiner*—Irina S. Zemel
*Attorney, Agent, or Firm*—Foley, Hoag & Eliot LLP; Matthew P. Vincent; Beth E. Arnold

[57] ABSTRACT

The present invention relates a process for stereoselective or regioselective chemical synthesis which generally comprises reacting a nucleophile and a chiral or prochiral cyclic substrate in the presence of a non-racemic chiral catalyst to produce a steroisomerically or regioselectively enriched product.

82 Claims, No Drawings

OTHER PUBLICATIONS

Goves, J. and R. Neumann (1989) "Regioselective Oxidation Catalysis In Synthetic Phospholipid Vesicles. Membrane–Spanning Steroidal Metalloporphyrins" *J. Am. Chem. Soc.* 111:2900–2909.

Groves, J. and R. Neumann (1987) "Membrane–Spanning Steroidal Metalloporphyrins as Site–Selective Catalysts in Synthetic Vesicles" *J. Am. Chem. Soc.* 109:5045–5047.

Jameson, D. (1990) "2,6–Bis(N–pyrazolyl)pyridines: The Convenient Synthesis Of A Family Of Planar Tridentate N3 Ligands That Are Terpyridine Analogues" *J. Org. Chem.* 55:4992–4994.

Jocobsen, E. et al. (1991) "Highly Enantioselective Epoxidation Catalysts Derived From 1,2–Diaminocyclohexane" *J. Am. Chem. Soc.* 113:7063–7064.

Knebel, W. and R. Angelici (1974) "Kinetic and Equilibrium Studies of Bi–and Tridentate Chelate Ring–Opening Reactions of Metal Carbonyl Complexes" *Inorganic Chemistry* 13(3):632–637.

Kruper, W. and Dellar, D. (1995) "Catalytic Formation of Cyclic Carbonates From Epoxides and CO2 With Chromium Metalloporphyrinates" *J. Org. Chem.* 60:725–727.

Larrow, J. and E. Jacobsen (1994) "Kinetic Resolution Of 1,2,–Dihydronaphthalene Oxide And Related Epoxides Via Asymmetric C–H Hydroxylation" *J. Am. Chem. Soc.* 116:12129–12130.

Larrow, J. and E. Jacobsen (1994) "A Practical Method For The Large–Scale Preparation Of [N,N'–Bis(3,5–di–tert–butylsalicylidene)– 1,2–Cyclohexanediaminato (2–)]manganese (III) Chloride, A Highly Enantioselective Epoxidation Catalyst" *J. Org. Chem.* 59:1939–42.

Li, Z. et al. (1993) "Asymmetric Alkene Aziridination with Readily Available Chiral Diimine–Based Catalysts" *J. Am. Chem Soc.* 115(12):5326–5327.

Marangoni, G. and B. Pitteri (1993) "Crystal Structure Of Cationic Square Planar Platinum(II) Complexes Containing The Tridentate Chelate Ligand 2,6–Bis(methylthiomethyl)pyridine" *Polyhdron* 12(13):1669–1673.

Maruoka, K et al. (1989) "An Efficient, Catalytic Procedure For Epoxide Rearrangement" *Tetrahedron Letters* 30(41):5607–5610.

Narasak, K. (1991) "Chiral Lewis Acids In Catalytic Asymmetric Reactions" *Synthesis* Jan.:1–11.

Nugent, W. (1993) "Beyond Nature's Chiral Pool: Enantioselective Catalysis In Industry" *Science* 259:479–483.

Nugent, W. et al. (1992) "Chiral Lewis Acid Catalysis. Enantioselective Addition of Azide to Meso Epoxides" *J. Am. Chem. Soc.* 114:2768–2769.

Oppolzer, W. and R. Radinov (1988) "Enantioselective Synthesis Of Sec–Allylalcohols By Catalytic Asymmetric Addition Of Divinylzinc To Aldehydes" *Tetrahedron Letters* 29(44):5645–5648.

Ozaki, S. et al. (1990) "Synthesis Of Chiral Square Planar Cobalt(III) Complexes and Catalytic Asymmetric Epoxidations With There Complexes" *J. Chem. Soc. Perkin Trans. 2* Issue 1:353–359.

Palucki, M. et al. (1994) "Highly Enantioselective, Low–Temperature Epoxidation of Styrene" *J. Am. Chem. Soc.* 116:9333–9334.

Palucki, A. et al. (1992) "Asymmetric Oxidation Of Sulfides With H2O2 Catalyzed By (Salen) Mn (III) Complexes" *Tetrahedron Letters*, 33(47):7111–7114.

Sasaki, H. et al. (1994) "Rational Design Of Mn–Salen Catalyst (2): Highly Enantioselective Epoxidation of Conjugated cis–Olefins" *Tetrahedron*50(41):11827–11838.

Schurig, V. and F. Betschinger (1992) "Metal–Mediated Enantioselective Access to Unfunctionalized Allphatic Oxiranes: Prochiral and Chiral Recognition" *Chem. Rev.* 92:873–888.

Srinivasan, K. et al. (1986) "Epoxidation of Olefins With Cationic (Salen) Mn III Complexes. The Modulation of Catalytic Activity By Substituents" *J. Am. Chem. Soc.* 108:2309–2320.

Stinson, S. (1992) "Chiral Drugs" *Chemical and Chemical Engineering News* Sep. 28 p. 46–79.

Ward, R. (1990) "Non–Enzymatic Asymmetric Transformations Involving Symmetrical Bifunctional Compounds" *Chem. Soc. Rev.*19:1–19.

Woolley, P. (1975) "Models For Metal Ion Function In Carbonic Anhydrase" *Nature*258:677682.

Yamashita, H. (1988) "Metal(II) d–Tartrates Catalyzed Asymmetric Ring Opening Of Oxiranes With Various Nucleophiles" *The Chemical Society of Japan* 61:1213–1220.

Zhang, W. et al. (1990) "Enantioselective Epoxidation Of Unfunctionalized Olefins Catalyzed By (Selen)manganese Complexes" *J. Am. Chem. Soc.* 112:2801–2803.

Zhang, W. and E. Jacobsen (1991) "Asymmetric Olefin Epoxidation With Sodium Hypochlorite Catalyzed By Easily Preparted Chiral Mn (III) Salen Complexes" *J. Org. Chem.* 56:2296–2298.

STEREOSELECTIVE RING OPENING REACTIONS

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sept. 28, 1992, pp. 46–79) include fewer side effects and greater potency of enantiomerically pure compounds.

Traditional methods of organic synthesis have often been optimized for the production of racemic materials. The production of enantiomerically pure material has historically been achieved in one of two ways: use of enantiomerically pure starting materials derived from natural sources (the so-called "chiral pool"), or resolution of racemic mixtures by classical techniques. Each of these methods has serious drawbacks, however. The chiral pool is limited to compounds found in nature, so only certain structures and configurations are readily available. Resolution of racemates requires the use of resolving agents, which may be inconvenient and time-consuming. Furthermore, resolution often means that the undesired enantiomer is discarded, thus wasting half of the material.

Epoxides are valuable intermediates for the stereocontrolled synthesis of complex organic compounds due to the variety of compounds which can be obtained by epoxide-opening reactions. For example, α-amino alcohols can be obtained simply by opening of an epoxide with azide ion, and reduction of the resulting α-azido alcohol (for example, by hydrogenation). Reaction of other nucleophiles similarly yields functionalized compounds which can be converted to useful materials. A Lewis acid may be added to act as an epoxide-activating reagent.

The utility of epoxides has expanded dramatically with the advent of practical asymmetric catalytic methods for their synthesis (Johnson, R. A.; Sharpless, K. B. In *Catalytic Asymmetric Synthesis*. Ojima, I., Ed.: VCH: New York, 1993; Chapter 4.1. Jacobsen, E. N. *Ibid*. Chapter 4.2). In addition to epoxidation of prochiral and chiral olefins, approaches to the use of epoxides in the synthesis of enantiomerieally enriched compounds include kinetic resolutions of racemic epoxides (Maruoka, K.; Nagahara, S.; Ooi, T.; Yamamoto, H. *Tetrahedron Lett* 1989, 30, 5607. Chen, X.-J.; Archelas, A.; Rurstoss, R. *J Org Chem* 1993, 58, 5528. Barili, P. L.; Berti, G.; Mastrorilli, E. *Tetrahedron* 1993, 49, 6263.)

A particularly desirable reaction is the asymmetric ring-opening of symmetrical epoxides, a technique which utilizes easily made achiral starting materials and can simultaneously set two stereogenic centers in the functionalized product. Although the asymmetric ring-opening of epoxides with a chiral reagent has been reported, in most previously known cases the enantiomeric purity of the products has been poor. Furthermore, many previously reported methods have required stoichiometric amounts of the chiral reagent, which is likely to be expensive on a large scale. A catalytic asymmetric ring-opening of epoxides has been reported (Nugent, W. A., *J Am Chem Soc* 1992, 114, 2768); however, the catalyst is expensive to make. Furthermore, good asymmetric induction (>90% e.e.) was observed only for a few substrates and required the use of a Lewis-acid additive. Moreover, the catalytic species is not well characterized, making rational mechanism-based modifications to the catalyst difficult.

SUMMARY OF THE INVENTION

In one aspect of the present invention, there is provided a process for stereoselective chemical synthesis which generally comprises reacting a nucleophile and a chiral or prochiral cyclic substrate in the presence of a non-racemic chiral catalyst to produce a stereoisomerically enriched product. The cyclic substrate comprises a carbocycle or heterocycle having a reactive center susceptible to nucleophilic attack by the nucleophile, and the chiral catalyst comprises an asymmetric tetradentate or tridentate ligand complexed with a metal atom. In the instance of the tetradentate ligand, the catalyst complex has a rectangular planar or rectangular pyrimidal geometry. The tridentate ligand-metal complex assumes a planar geometry. In a preferred embodiment, the ligand has at least one schiff base nitrogen complexed with the metal core of the catalyst. In another preferred embodiment, the ligand provides at least one stereogenic center within two bonds of an ligand atom which coordinates the metal.

In general, the metal atom is a transition metal from Groups 3–12 or from the lanthanide series, and is preferably not in its highest state of oxidation. For example, the metal can be a late transition metal, such as selected from Group 5–12 transition metals. In preferred embodiments, the metal atom is selected from the group consisting of Cr, Mn, V, Fe, Mo, W, Ru and Ni.

In preferred embodiments, the substrate is represented which is acted on by the nucleophile is represented by the general formula 118:

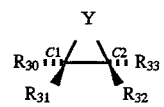

in which

Y represents O, S, N(R$_{50}$), C(R$_{52}$)(R$_{54}$), or has the formula A—B—C; wherein R$_{50}$ represents a hydrogen, an alkyl, a carbonyl-substituted alkyl, a carbonyl-substituted aryl, or a sulfonate, R$_{52}$ and R$_{54}$ each independently represent an electron-withdrawing group; A and C are independently absent, or represent a C$_1$–C$_5$ alkyl, O, S, carbonyl, or N(R$_{50}$); and B is a carbonyl, a thiocarbonyl, a phosphoryl, or a sulfonyl; and R$_{30}$, R$_{31}$, R$_{32}$, and R$_{33}$ represent organic or inorganic substituent which form a covalent bond with the C1 or C2 carbon atoms of 118, and which permit formation of a stable ring structure including Y. For instance, the substituents R$_{30}$, R$_{31}$, R$_{32}$, and R$_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —(CH$_2$)$_m$—R$_7$; or any two or more of the substituents R$_{30}$, R$_{31}$, R$_{32}$, and R$_{33}$ taken together form a carbocylic or heterocyclic ring having from 4 to 8 atoms in the ring structure. In this formula, R$_7$ represents an aryl, a cycloalkyl, a cycloalkenyl, a heterocycle or a polycycle; and m is zero or an integer in the range of 1 to 8. In certain embodiments, R$_{30}$, R$_{31}$, R$_{32}$, and R$_{33}$ are chosen such that the substrate has a plane of symmetry.

Exemplary cyclic substrate for the subject reaction include epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

In a preferred embodiment, the method includes combining a nucleophilic reactant, a prochiral or chiral cyclic substrate, and a non-racemic chiral catalyst as described herein, and maintaining the combination under conditions appropriate for the chiral catalyst to catalyze stereoselective opening of the cyclic substrate at the electrophilic atom by reaction with the nucleophilic reactant.

In preferred embodiments, the chiral catalyst which is employed in the subject reaction is represented by the general formula:

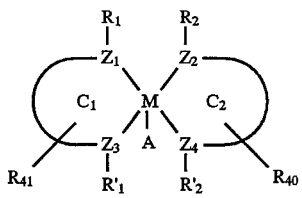

in which $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents the late transition metal; and

A represents a counterion or a nucleophile, wherein each $R_1$, $R_2$, $R'_1$, $R'_2$ $R_{40}$ and $R_{41}$ are selected to provide at least one stereogenic center in the tetradentate ligand.

In exemplary embodiments, $R_1$, $R_2$, $R'_1$ and $R'_2$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

each $R_{40}$ and $R_{41}$ occuring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

$R_7$ represents an aryl, a cycloalkyl, a cycloalkenyl, a heterocycle or a polycycle;

$Z_1$, $Z_2$, $Z_3$ and $Z_4$ are independently selected from the group consisting of nitrogen, oxygen, phosphorus, arsenic, and sulfur; and m is zero or an integer in the range of 1 to 8.

For example, the catalyst can be represented by the general formula:

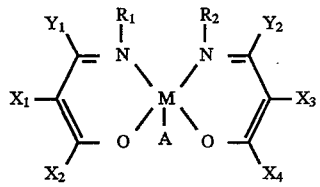

in which the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, or any two or more of the substituents taken together form a carbocyle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocabonyls to which they are attached as a tetradentate ligand, and at least one of $Y_1$ and $Y_2$ is a hydrogen;

$R_7$ represents an aryl, a cycloalkyl, a cycloalkenyl, a heterocycle, or a polycycle;

m is zero or an integer in the range of 1 to 8;

M represents the late transition metal; and

A represents a counterion or a nucleophile, wherein each of of substituents $R_1$, $R_2$, $Y_1$, $Y_2$, $X_1$, $X_2$, $X_3$ and $X_4$, are selected such that the catalyst is asymmetric.

For example, a preferred class of catalysts are represented by the general formula:

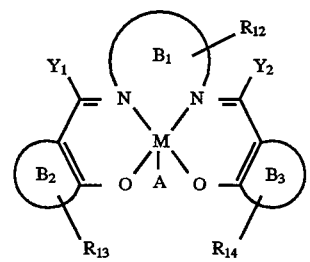

in which the $B_1$ moiety represents a diimine bridging substituent represented by —$R_{15}$—$R_{16}$—$R_{17}$—, wherein $R_5$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sufonyl, a selenium, a carbonyl, or an ester; each of $B_2$ and $B_3$ independently represent rings selected from a group consisting of cycloalkyls, cycloakenyls, aryls, and heterocyclic rings, which rings comprising from 4 to 8 atoms in a ring structure;

$Y_1$ and $Y_2$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, wherein $R_{12}$ can occur on one or more positions of —$R_{15}$—$R_{16}$—$R_{17}$—, or any two or more of the $R_{12}$, $R_{13}$, $R_{14}$, $Y_1$ and $Y_2$ taken together form a bridging substituent;

$R_7$ represents an aryl, a cycloalkyl, a cycloalkenyl, a heterocycle, or a polycycle;

m is zero or an integer in the range of 1 to 8;

M represents a transition metal; and

A represents a counterion or a nucleophile, wherein $R_{12}$, $R_{13}$, $R_{14}$, $Y_1$ and $Y_2$ are selected such that the catalyst is asymmetric.

In yet further preferred embodiments, the catalyst is a metallosalenate catalyst represented by the general formula:

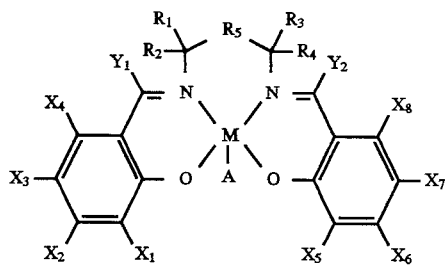

in which each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents taken together form a carbocycle or heterocycle having from 4 to 10 atoms in the ring structure;

$R_7$ represents an aryl, a cycloalkyl, a cycloalkenyl, a heterocycle or a polycycle;

m is zero or an integer in the range of 1 to 8;

M represents a transition metal; and

A represents a counterion or a nucleophile;

wherein if $R_5$ is absent, at least one of $R_1$ and $R_2$ is taken together with at least one of $R_3$ and $R_4$ to form a bridging substituent, and each of of the substituents of 106 are selected such that the salenate is asymmetric.

Alternatively, the catalyst can have a tridentate ligand, such as the ligand represented by the general formula:

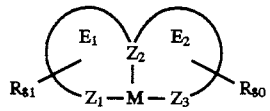

in which $Z_1$, $Z_2$, and $Z_3$ each represent a Lewis base;

the $E_1$ moiety, taken with $Z_1$, $Z_2$ and M, and the $E_2$ moiety, taken with $Z_2$, $Z_3$ and M, each, independently, form a heterocycle;

$R_{80}$ and $R_{81}$ each independently are absent, hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, or any two or more of the $R_{80}$ and $R_{81}$ substituents taken together form a bridging substituent;

$R_7$ represents an aryl, a cycloalkyl, a cycloalkenyl, a heterocycle or a polycycle;

m is zero or an integer in the range of 1 to 8;

M represents a transition metal; and

A represents a counteranion or a nucleophile, wherein the tridentate ligand is asymmetric.

As described herein, the subject method can be used for carrying out enantioselective ring opening, diastereoselective ring opening (including kinetic resolution) as well as expanding a ring of a cyclic compound.

DETAILED DESCRIPTION OF THE INVENTION

The ability to introduce a stereocenter selectively or to resolve a racemic mixture has broad application, especially in the agricultural and pharmaceutical industries, as well as in the polymer industry. As described herein, the present invention makes available methods and reagents for stereoselective and regioselective synthesis involving nucleophile-mediated ring opening reactions. The primary constituents of the method, set out in more detail below, are a chiral metal catalyst of particular tetradentate or tridentate geometry; a chiral or prochiral "substrate" including a carbocycle or heterocycle moiety with at least one electrophilic ring atom; and a nucleophilic reactant which is desired to be added at the site of the electrophilic ring atom.

I. Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as amines, mercaptans and alcohols, and charged moieties such as alkoxides, thiolates, carbanions, and a variety of organic and inorganic artions. Illustrative artionic nucleophiles include simple anions such as azide, cyanide, thiocyanate, acetate, formate or chloroformate, and bisulfite. Organometallic reagents such as organocuprates, organozincs, organolithiums, Grignard reagents, enolates, acetylides, and the like may, under approriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "eleetrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The term "ring expansion" refers to a process whereby the number of atoms in a ring of a cyclic compound is increased. An illustrative example of ring expansion is the reaction of epoxides with $CO_2$ to yield cyclic carbonates.

The term "meso compound" is recognized in the art and means a chemical compound which has at least two chiral centers but is achiral due to a plane of symmetry.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which hive the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "complex" as used herein and in the claims means a coordination compound formed by the union of one or more electronically rich molecules or atoms capable of independent existence with one or more electronically poor molecules or atoms, each of which is also capable of independent existence.

The term "substrate" is intended to mean a chemical compound which can react with a nucleophile, or with a ring-expansion reagent, according to the present invention, to yield at least product having a stereogenic center.

The term "catalytic amount" is recognized in the art and means a substoichiometric amount of catalyst relative to a reactant. As used herein, a catalytic amount means from 0.0001 to 90 mole percent catalyst relative to a reactant, more preferably from 0.001 to 50 mole percent, still more preferably from 0.01 to 10 mole percent, and even more preferably from 0.1 to 5 mole percent catalyst to reactant.

As discussed more fully below, the reactions contemplated in the present invention include reactions which are enantioselective, diastereoselective, or regioselective. An enantioselective reaction is a reaction which converts an achiral reactant to a chiral, nonracemic product enriched in one enantiomer. Enantioselectivity is generally quantified as "enantiomeric excess" ("e.e.", sometimes referred to as "optical pity" or "optical activity"), defined as follows:

$$e.e. = \left[ \frac{(A-B)}{(A+B)} \right] \times 100$$

where A and B are the amounts of the enantiomers formed. An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This is termed a kinetic resolution, wherein the reactant enantiomers are resolved by differential reaction rate to yield an enantiomerically enriched product. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another reactive center. For example, a regioselective reaction of an unsymmetrically substituted epoxide substrate would cause preferential reaction at one of the two epoxide ring carbons.

The term "non-racemic" with respect to the chiral catalyst, means a preparation of catalyst having greater than 50% of a desired stereoisomer, more preferably at least 75%. "Substantially non-racemic" refers to preparations of the catalyst which have greater than 90% ee for a desired stereoisomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl, an alkoxyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —$CN$ and the like. Exemplary substitued alkyls are described below. Cycloalkyls can be further substituted with alkyls, alkenyls, alkoxys, thioalkyls, aminoalkyls, carbonyl-substituted alkyls, $CF_3$, $CN$, and the like.

The terms "alkenyl" and "alkynyl" refer to unsaturated aliphatic groups analogous in length and possible substitution to the alkyls described above, but which contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —$F$, —$Cl$, —$Br$ or —$I$; the term "thiol" means —$SH$; the term "hydroxyl" means —$OH$; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

Thus, the term "alkylamine" as used herein means an alkyl group, as defined above, having a substituted or unsubstituted amine attached thereto. In exemplary embodiments, an "amine" can be represented by the general formula:

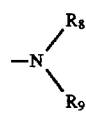

wherein $R_8$ and $R_9$ each independently represent a hydrogen, an alkyl, an alkenyl, —$(CH_2)_m$—$R_7$, —$C(=O)$-alkyl, —$C(=O)$-alkenyl, —$C(=O)$-alkynyl, —$C(=O)$—$(CH_2)_m$—$R_7$, or $R_8$ and $R_9$ taken together with the N atom to which they are attached complete a heterocycle having from 4 to 8 atoms in the ring structure; $R_7$ represents an aryl, a cycloalkyl, a cycloalkenyl, a heterocycle or a polycycle; and m is zero or an integer in the range of 1 to 8.

Likewise, the term "alkylamide" refers to an alkyl group having a substituted or unsubstituted amide group attached thereto. For instance, an "amide" can be represented by the general formula:

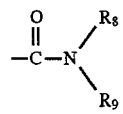

wherein $R_8$ and $R_9$ are as defined above.

The term "akylimine" refers to an alkyl group having a substituted or unsubstituted imine attached thereto. An "imine" can be represented by the general formula:

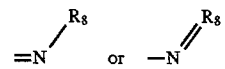

wherein $R_8$ is as described above.

The term "thioalkyl" refers to an alkyl group, as defined above, having a sulfhydryl or thioether group attached thereto. In preferred embodiments, the "thioether" moiety is represented by one of —S-alkyl, —S-alkenyl, —S-alkynyl, and —S—$(CH_2)_m$—$R_7$, wherein m and $R_7$ are defined above.

The term "carbonyl-substituted alkyl" as used herein means an alkyl group, as defined above, having a substituted or unsubstituted carbonyl group attached thereto, and includes aldehydes, ketones, carboxylates and esters. In exemplary embodiments, the "carbonyl" moiety is represented by the general formula:

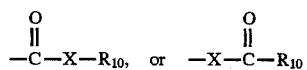

wherein X is absent or represents an oxygen or a sulfur, and $R_{10}$ represents a hydrogen, an alkyl, an alkenyl, or —$(CH_2)_m$—$R_7$, where m and $R_7$ are as defined above. Where X is an oxygen, the formula represents an "ester". Where X is a sulfur, the formula represents a "thioester." Where X is absent, and $R_{10}$ is not hydrogen, the above formula represents a "ketone" group. Where the oxygen atom of the above formula is replaced by sulfur, the formula represents a "thiocarbonyl" group.

The terms "alkoxyl" or "alkoxy" as used herein refers to an alkyl group, as defined above, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl which renders that alkyl an ether is or resembles an alkoxyl, such as can be represented by one of —O-alkyl, —O-alkenyl, —O-alkynyl, —O—$(CH_2)_m$—$R_7$, where m and $R_7$ are described above.

Thus, the term "phosphorylalkyl" as used herein means an alkyl group, as defined above, having a substituted or unsubstituted phosphoryl group attached thereto. A "phosphoryl" can in general be represented by the formula:

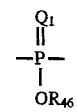

wherein $Q_1$ represented S or O, and $R_{46}$ represents hydrogen, a lower alkyl or an aryl. When used to substitute an akyl, the phosphoryl group of the phosphorylalkyl can be represented by the general formula:

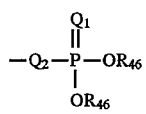

wherein $Q_1$ represented S or O, and each $R_{46}$ indepedently represents hydrogen, a lower alkyl or an aryl, $Q_2$ represents O, S or N.

The term "metalloalkyl" refers to an alkyl group, as defined above, having a substituted or unsubstituted organometallic group attached thereto: A "silyl alkyl" is an alkyl having a substituted silicon attached thereto. In a preferred embodiment, the "silyl" moiety which may be substituted on the alkyl can be represented by the general formula:

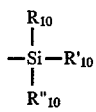

wherein $R_{10}$, $R'_{10}$ and $R''_{10}$ independently represent a hydrogen, an alkyl, an alkenyl, or —$(CH_2)_m$—$R_7$, m and $R_7$ being defined above.

Likewise, a "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

The term "sulfonate" as used herein means a sulfonyl group, as defined above, attached to an alkyl or aryl group. Thus, in a preferred embodiment, a sulfonate has the structure:

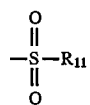

in which $R_{11}$ is an alkyl or an aryl.

The term sulfate, as used herein, means a sulfonyl group, as defined above, attached to a hydroxy or alkoxy group. Thus, in a preferred embodiment, a sulfate has the structure:

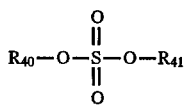

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonites, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

A "bridging substituent" refers to a substitution at two (or more) sites on the core structure of the catalyst by the same (as opposed to identical) substituent so as to form a covalent bridge between the substitution sites. For example, a bridging substituent may be represented by the general formula or —$R_{15}$—$R_{16}$—$R_{17}$—, wherein $R_{15}$ and $R_{17}$ each independently are absent or represent an alkyl, an alkenyl, or an alkynyl, preferably $C_1$ to $C_{10}$, and $R_{16}$ is absent or represents an amine, an imine, an amide, a phosphoryl a carbonyl, a silyl, an oxygen, a sulfonyl, a sulfer, a selenium, or an ester. Exemplary bridging substituents are given by the "picnic basket" forms of, for instance, the porphoryn catalysts described below.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

II. Catalyzed Reactions

In one aspect of the present invention there is provided a process for stereoselectively producing compounds with at least one stereogenic center. An advantage of this invention is that enantiomerically enriched products can be synthesized from achiral or racemic reactants. Another advantage is that yield losses associated with the production of an undesired enantiomer can be substantially reduced.

In general, the invention features a stereoselective ring opening process which comprises combining a nucleophilic reactant, a prochiral or chiral cyclic substrate, and at least a catalytic amount of non-racemic chiral catalyst of particular characteristics (as described below). The cyclic substrate of the reaction will include a carbocycle or heterocycle which has an electrophilic atom susceptible to attack by the nucleophile. The combination is maintained under conditions appropriate for the chiral catalyst to catalyze stereoselective opening of the cyclic substrate at the electrophilic atom by reaction with the nucleophilic reactant. This reaction can be applied to enatioselective processes as well as diastereoselective processes. It may also be adapted for regioselective reactions. Examples of enantioselective reactions, kinetic resolution, and regioselective reactions which may be catalyzed according to the present invention follow.

In an exemplary embodiment, an epoxide ring can be opened with a nucleophile, e.g., trimethylsilyl azide (TMS-N$_3$), in the presence of a chiral catalyst of the subject reaction.

such as the three carbocyclic nucleoside analogs shown below, some of which are in clinical trials.

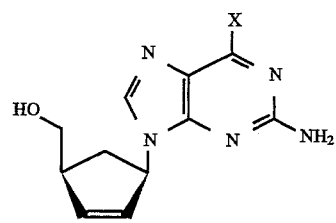

X = OH: Carbovir

X = NH—◁ : 1592U89

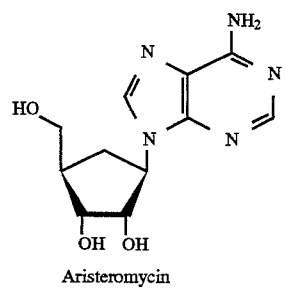

Aristeromycin

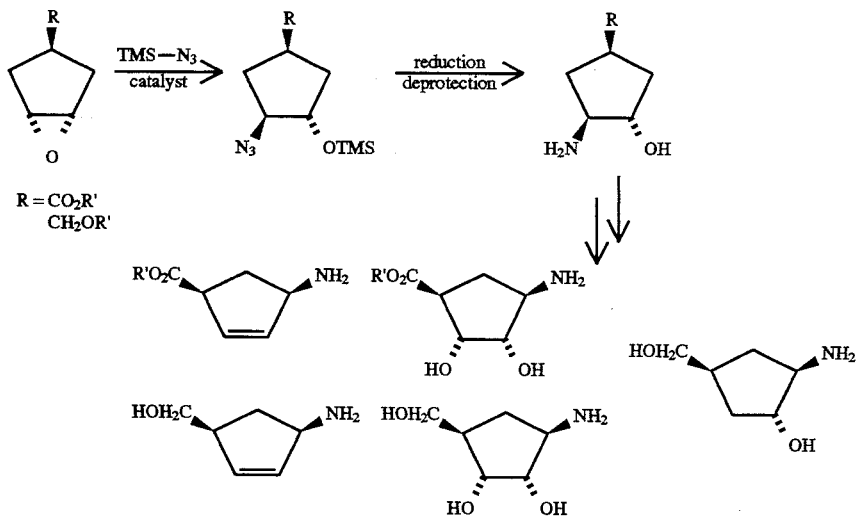

The opening of a meso epoxide in the presence of a chiral catalyst yields an enantiomerically enriched silyl azidoalcohol, which can then be transformed, through standard manipulations, to a variety of products, a few examples of which are shown above. These products are useful for the synthesis of compounds with potential antiviral activity,

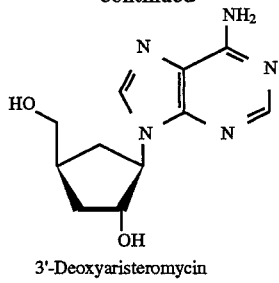

3'-Deoxyaristeromycin

The present invention also provides a practical method of synthesizing precursors for prostaglandins, including key intermediates used for the commercial production of prostaglandins. As shown below, the ring-opening of a meso epoxide produces an enantiomerically enriched product which is easily converted to a useful intermediate.

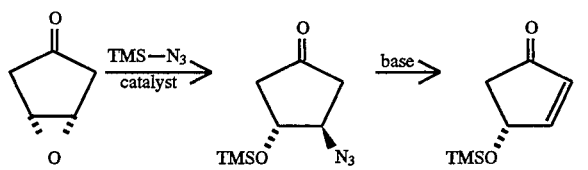

In another illustrative embodiment, the present invention provides a method for synthesizing balanol, a potent protein kinase C inhibitor, as shown below.

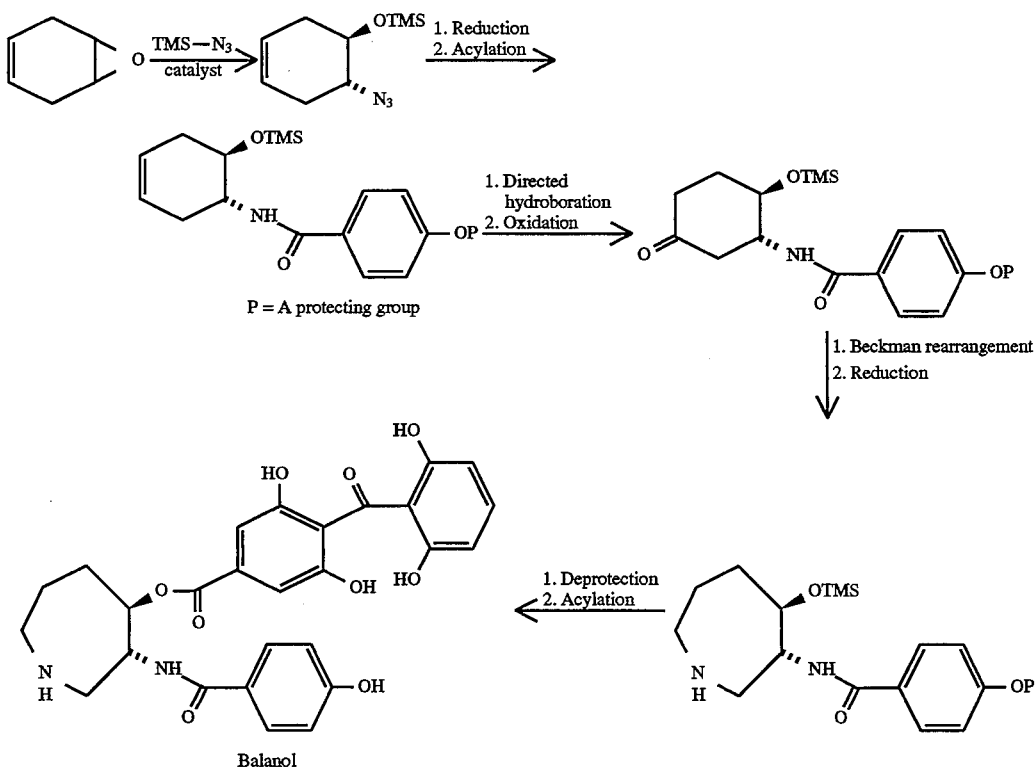

In yet another exemplary embodiment, the subject reaction can be used to catalyze the stereoselective ring-opening of an aziridine, such as with the nucleophile ammonia exemplified below:

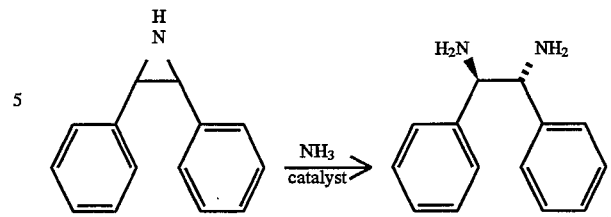

In this case, the chiral diamines are useful in, for example, synthesis of certain of the chiral ligands of the catalyst described herein. For instance, such chiral diamines can be used to make metallosalenate catalysts for use in the method of the present invention.

The ring-opening of an episulfide with an amine in the presence of a chiral catalyst, shown below, is another exemplary reaction of the subject method which can be carried out stereoselectively.

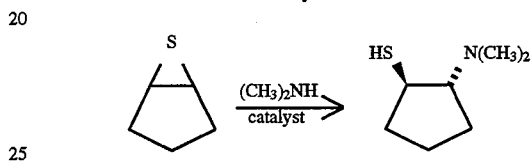

The product amino thiols are useful in, for example, the synthesis of penicillin analogs.

In another embodiment, the opening of a cyclic sulfate with an acetylide can be carried out in the presence of a chiral catalyst of the subject method, such as illustrated below:

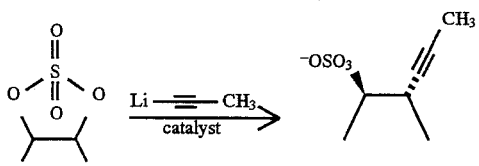

The sulfate group of the product can be removed to reveal the homopropargylic alcohol, or can be used as a protecting group in further synthesis.

Still another ring-opening reaction contemplated by the present method is the opening of a cyclopropane by a mercaptan in the presence of one of the subject chiral catalyst:

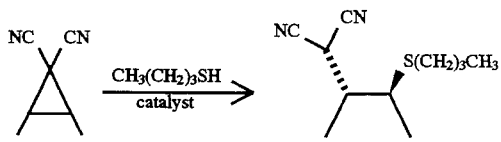

The product may be converted, for example, to a 3,4-substituted carboxylic acid by hydrolysis and decarboxylation.

In certain embodiments, the subject reaction can be used for a reaction involving intramolecular ring-opening. For instance, as illustrated below, an epoxide can be opened by an alcohol moiety of the same molecule in the presence of a chiral catalyst in accordance with the present method:

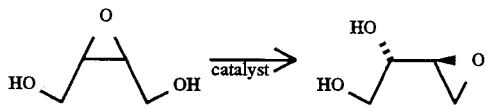

The product 1,2-epoxy diol can easily be converted to a variety of natural and non-natural products such as sugars and sugar analogs.

Still another exemplary ring-opening scheme of the present invention is generally illustrated below by the opening of a cyclic carbonate with an amine:

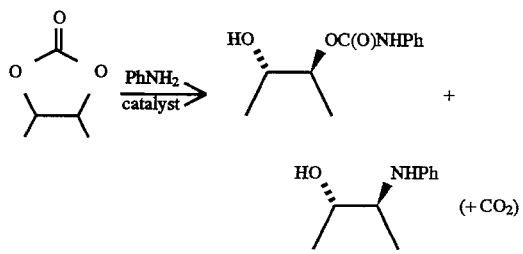

It will be understood that two different products may result from this ring opening, depending on whether nucleophilic attack at the carbonyl carbon or the hydroxylic carbon is favored. The ratio of products can be adjusted to favor one or the other by manipulation of such factors as the nucleophile, the chiral catalyst, and the reaction conditions employed. Both products can be converted to synthetically useful products by conventional methods.

Still another enantioselective reaction is demonstrated by the ring-opening of an epoxide by an organocopper reagent in the presence of a chiral catalyst, as is shown below:

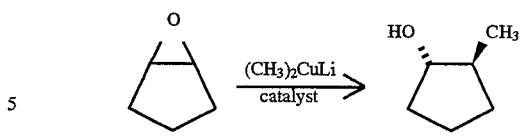

In another aspect of the present invention, kinetic resolution of enantiomers occurs by catalysis with a chiral catalyst of a ring-opening reaction of a racemic substrate. In the subject metal-mediated kinetic resolution process for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than the expensive, enantiomerically pure starting compounds. For example, propylene oxide is a versatile reagent for introduction of a functionalized three-carbon unit into a molecule. However, the pure (S)-propylene oxide is very expensive, costing up to 300 times more than the racemic mixture. Thus, although kinetic resolution according to the present method may result in the waste of half of the reagent, large cost savings may be realized by use of the racemic mixture. Examples of such kinetic resolutions are shown below.

For instance, catalyst-mediated kinetic resolution of chiral oxiranes (e.g. chiral recognition) described herein represent important alternate approaches to asymmetric epoxidation (prochiral recognition) processes of the prior art because racemic oxiranes are easily accessible and often produced at a large industrial scale rendering the loss of 50% of the antipode acceptable. Stereoselectivity in the kinetic resolution of oxiranes by the subject reaction processes is determined by the chirality of the catalyst.

In an exemplary embodiment, the kinetic resolution of a racemic epoxide is shown below.

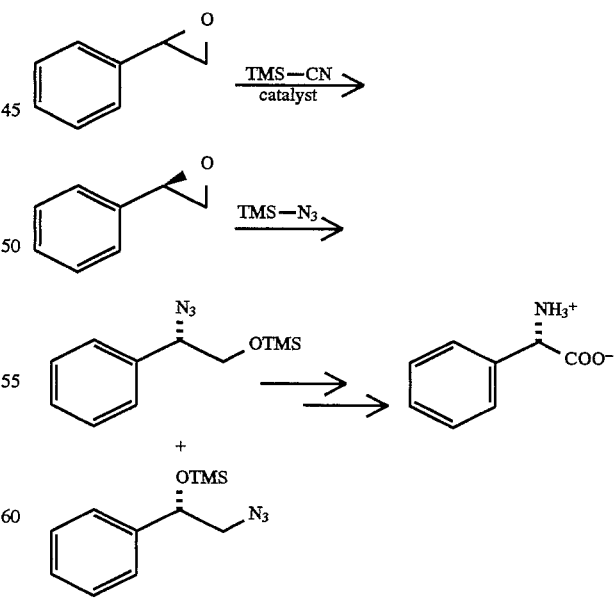

One enantiomer of styrene epoxide is preferentially consumed by trimethylsilyl cyanide in the presence of a chiral catalyst. The remaining enantiomer is then reacted with TMS-azide to yield either of a pair of silyl azidoalcohols. The desired isomer can be made the major product by choice of appropriate reaction conditions. The α-phenylazide isomer can be converted, through conventional reactions, to the amino acid (S)-phenylglycine. The ability to carry out this conversion has significant commercial value since optically active amino acids and amino acid analogs are biologically important and have many agricultural and pharmaceutical Still another example of kinetic resolution with a reaction of the present invention involves the synthesis of juvenile hormone. In the reaction scheme:

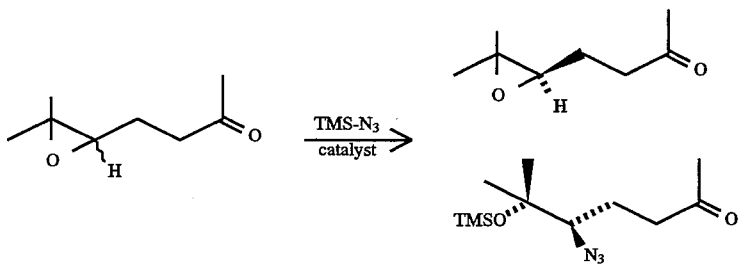

applications. The β-phenylazide isomer can also be converted to pharmaceutically useful products.

Ring-opening of cyclic sulfates by amines, followed by treatment with a base, is a useful method of producing aziridines, as disclosed in U.S. Pat. No. 5,321,143 to Sharpless. Thus, ring-opening of a racemic chiral cyclic sulfate with an amine, in the presence of a chiral catalyst according to the present invention, followed by treatment with a base, is a method of preparing enantiomerically enriched aziridines.

In another illustrative embodiment, the subject method can be used to provide enantiomerically enriched compounds useful in the synthesis of the anti-anginal drug diltiazem.

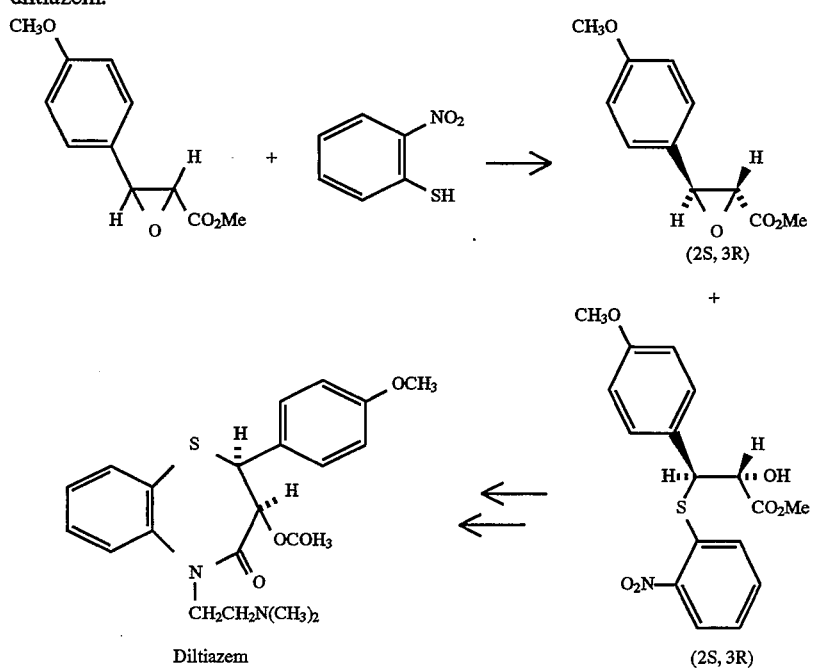

The racemic mixture of trans-epoxides is resolved by reaction with 2-nitrothiophenol in the presence of a chiral catalyst, and the enantiomerically enriched ring-opened product is separated from the unreacted epoxide. The ring-opened product is then transformed to diltiazem by standard techniques.

treatment of the racemic epoxide with TMS-azide or the like in the presence of one of the subject chiral catalyst which is enantioselective for the (S)-epoxide can yield, after separation, the optically pure (R)-epoxide.

In yet another illustrative embodiment, the subject method can be used for kinetic resolution of α-bisabolol stereoisomers during synthesis from epoxylimonene precursors. The (−)-α-bisabolol enantiomer is used on an industrial scale for the preparation of various skin-care creams, lotions and ointments because of its antiinflammatory, bactericidal, and anti-mycotic properties. In a representative reaction scheme:

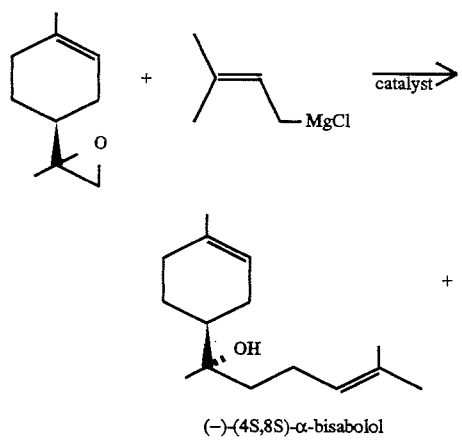

(−)-(4S,8S)-α-bisabolol a mixture coming (4S,8R)- and (4S,8S)-8,9-epoxy-p-menth-1-ene, obtained from 4(S)-limonene (Husstedt et al. (1979) *Synthesis* 966), is reacted with (3-methylbut-2-enyl)$_m$agnesium chloride in the presence of a chiral catalyst described herein. The resulting (−)-α-bisabolol can be isolated from the unreacted (4S,8R)-epoxide by, for example, flash chromatography. Alternatively, the racemic limonene epoxide mixture can be reacted with TMS-azide or the like in the presence of the antipodal chiral catalyst used in the illustrated reaction scheme in order to remove the (4S,8R)-epoxide, and subsequently reacting the remaining (4S,8S)-epoxide with (3-methylbut-2-enyl)$_m$agnesium chloride in the presence of copper iodide.

An another embodiment of a kinetic resolution reaction, there is provided a scheme for the ring-opening of a lactam with a nucleophile. For example, thiophenol can be reacted with a lactam in the presence of a chiral catalyst according to the present invention:

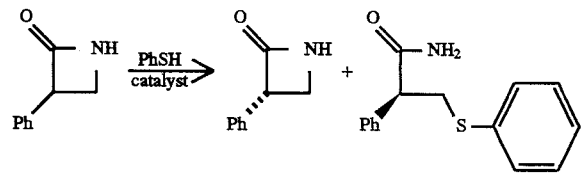

This aspect of the invention provides methods of easily synthesizing functionalized nonracemic products from inexpensive racemic starting materials. It will be noted that lactams have two potential modes of ring opening, viz. at the acyl carbon and at the nitrogen-bearing sp$^3$ carbon. Either mode is suitable for kinetic resolution according to the present invention. Which of the two modes of reaction will predominate will depend upon the particular substrate, nucleophile, catalyst, and reaction conditions employed, and can be determined and accordingly adjusted for the desired reaction by routine experimentation. In general, more highly strained, small-ring (e.g. 3- or 4-membered lactams) will be more likely to undergo cleavage at the sp$^3$ carbon.

In another illustrative embodiment, the present invention provides for the kinetic resolution of lactones by opening with such nucleophiles as a phenyl selenide anion in the presence of a chiral catalyst, as shown below:

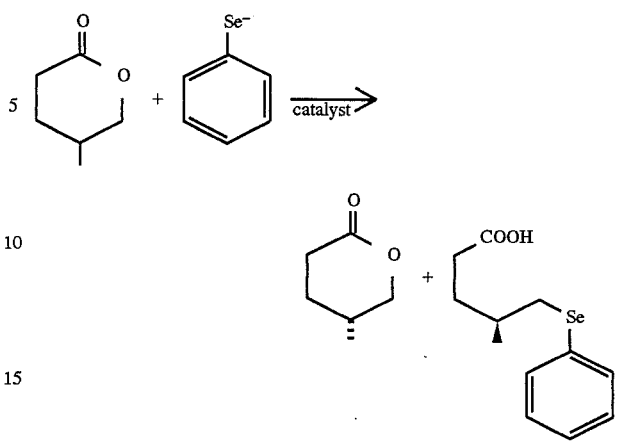

As with the lactam example shown above, two possible modes of ring-opening may operate to kinetically resolve the racemic substrate. As previously noted, more strained substrates will be more prone to undergo cleavage at the sp$^3$ carbon. However, certain nucleophiles, such as phenylselenide, are known to favor cleavage at the sp$^3$ carbon under appropriate conditions, even for larger ring lactones.

In another aspect of the present invention, kinetic resolution of enantiomers occurs by catalysis with a chiral catalyst of a ring expansion reaction of a racemic substrate. An example of such a kinetic resolution is shown below.

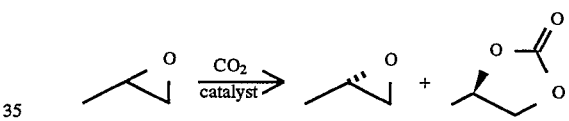

The racemic propylene oxide is resolved by reaction with carbon dioxide in the presence of a chiral catalyst. The resolved propylene oxide is a valuable reagent for use in synthesis of chiral materials, but is very expensive to purchase in enantiomerically pure form. The instant invention provides a highly economical method of producing such enantiomerically enriched materials.

In another aspect of the invention, kinetic resolution of diastereomers occurs by reaction of a diastereomeric mixture of a substrate with a nucleophile in the presence of a chiral catalyst. An illustrative example of such a diastereoselective reaction is shown below.

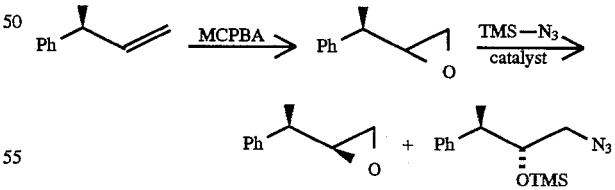

In this example, a mixture of diastereomers is generated by the epoxidation of a chiral alkene with MCPBA. The mixture of diastereomers is then resolved by reaction with trimethylsilyl azide in the presence of a chiral catalyst. The resolved diastereomers may then be easily separated. This method of resolution provides a simple means of separating diastereomers which may not be easily separated by other methods such as distillation or chromatography.

In another aspect of the invention, the reaction of a substrate with a nucleophile in the presence of a chiral catalyst occurs in a regioselective manner. An illustrative example of a regioselective reaction is shown below.

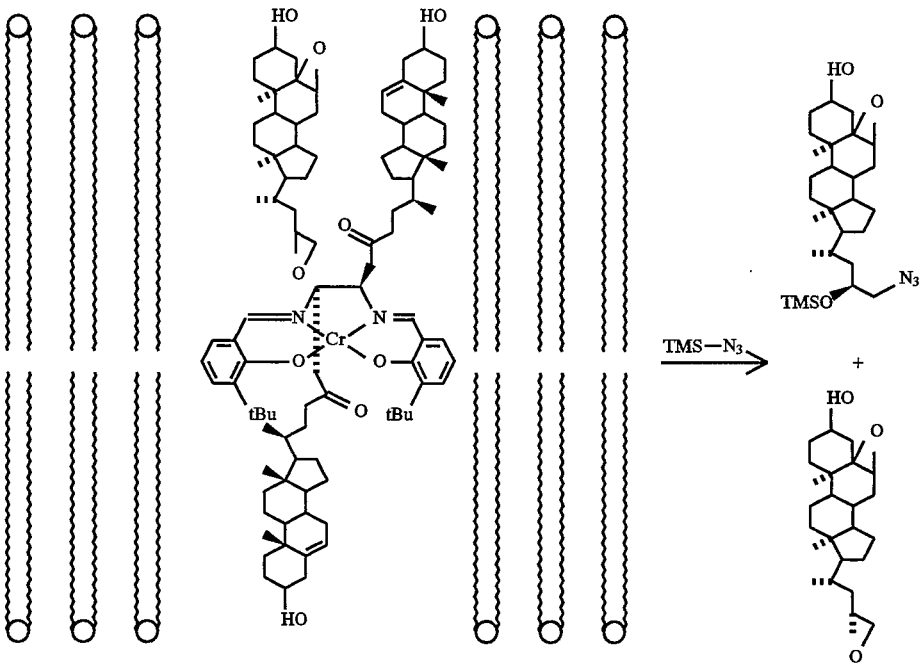

In this example, a steroidal bis-epoxide is reacted with trimethylsilyl azide in the presence of a chiral catalyst in a lipid bilayer. The chiral catalyst in this example is derivatized with steroidal groups, and can be further substituted with alkyl or other substituents to optimize the polarity of the catalyst and the selectivity of the reaction. Only one of the two epoxide moieties is opened by the nucleophile, and only one of the diastereomers is reactive. This reaction is therefore both regioselective and diastereoselective.

The processes of this invention can provide optically active products with very high stereoselectivity (e.g., enantioselectivity or diasteroseleetivity) or regioselectivity. In preferred embodiments of the subject enantioselective reactions, enantiomeric excesses of preferably greater than 50%, more preferably greater than 75% and most preferably greater than 90% can be obtained by the processes of this invention. Likewise, with respect to regioselective reactions, molar ratios for desired/undesired regioisomers of preferably greater than 5:1, more preferably greater than 10:1 and most preferably greater than 25:1 can be obtained by the processes of this invention. The processes of this invention can also be carried out at highly desirable reaction rates suitable for commercial use.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes, N-alkylation of amides, addition of aldehydes to amides, nitrile reduction, acylation of ketones by esters, acylation of amines and the like. To further illustrate, exemplary classes of pharmaceuticals which can be synthesized by a scheme including the subject stereoselective reaction are cardiovascular drugs, nonsteroidal antiinflammatory drugs, central nervous system agents, and antihistaminics.

III. Catalysts

The catalysts employed in the subject method involve chiral complexes which provide controlled steric environments for asymmetric opening of a carbocycle or heterocycle coupled, in certain preferred embodiments, with the generation of one or two new stereocenters upon reaction with a nucleophile. In general, catalysts intended by the present invention can be characterized in terms of a number of features. For instance, a salient aspect of each of the catalysts contemplated by the instant invention concerns the use of metalloligands which provide a rigid or semi-rigid environment near the catalytic site of the molecule. This feature, through imposition of structural rigidity on the chelated metal, can be used to establish selective approach of the substrate to the catalytic site and thereby induce stereoselectivity and/or regioselectivity in a ring opening reaction. Moreover, the ligand preferably places a restriction on the coordination sphere of the metal.

Another aspect of the catalyst concerns the selection of metal atoms for the catalyst. In general, any transition metal (e.g., having d electons) may be used to form the catalyst, e.g., a metal selected from one of Groups 3-12 of the periodic table or from the lanthanide series. However, in preferred embodiments, the metal will be selected from the group of late transition metals, e.g. preferably from Groups 5-12, in order to provide metal centers which are coordinatively unsaturated and not in their highest oxidation state. For example, suitable metals include Cr, Mn, V, Fe, Mo, W, Ru and Ni. Particularly preferred metals are from group 6, especially Cr(III).

A. Chiral Tetradentate Catalysts

Consistent with these desirable features, one class of particularly preferred chiral catalysts provide a chiral tetradentate ligand which coordinates a transition metal in a substantially square planar or square pyramidal geometry, though some distortion to these geometries is contemplated. Restated, these square geometries refer to tetradentate ligands in which the Lewis basic atoms lie substantially in the same plane, with the metal also in that plane (square planar), or above or below that plane (square pyramidal).

Preferred square tetradentate catalysts which may be employed in the subject reactions can be represented by the general formula 100:

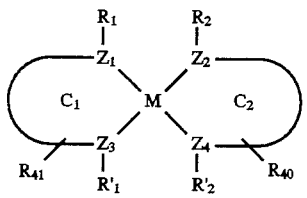

wherein $Z_1$, $Z_2$, $Z_3$ and $Z_4$ each represent a Lewis base, such as selected from the group consisting of nitrogen (e.g., imines, amines and amides), oxygen, phosphorus (e.g., phosphines or phosphinites), arsenic (arsines) and sulfur.

The $C_1$ moiety (taken with $Z_1$, $Z_3$ and M) and the $C_2$ moiety, (taken with $Z_2$, $Z_4$ and M) each, independently, form a heterocyclic ring. It will be understood that while the $C_1$ and $C_2$ structures depicted in the above formula may not formally be covalently closed rings for lack of a covalent bond with the metal M, for purposes of this disclosure, this and similar structures involving the metal catalyst atom M will nevertheless be referred to as heterocyclic rings, and substituents thereof will be referenced relative to heterocycle nomenclature (e.g., "fused rings" or "bridged rings"). In addition to substitutions at $R_1$, $R_2$, $R'_1$ and $R'_2$, the $C_1$ and $C_2$ rings can of course be substituted as appropriate at other ring positions, as illustrated by $R_{40}$ and $R_{41}$. Moreover, it will be appreciated that in certain embodiments two or more substituents of $C_1$ can be covalently bonded to each other to provide a fused ring or bridged ring including the $C_1$ ring atoms. Similar structures can be provided on the $C_2$ ring.

Accordingly, in the illustrated structure 100, $R_1$, $R_2$, $R'_1$ and $R'_2$ each independently are absent, or represent some substitution, as permitted by valence requirements, of the Lewis basic atoms, which substitution may be with hydrogen, halogens, alkyls, alkenyls, alkynyls, hydroxyl, amino, nitro, thio amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ substituents taken together can form a bridging substituent; with the proviso that at least one of $R_1$, $R'_1$ and $R_{41}$ forms a bridging substituent with at least one of $R_2$, $R'_2$ and $R_{40}$ in order to provide $C_1$ and $C_2$ as a tetradentate; $R_7$ represents an aryl, a cycloalkyl, a cycloalkenyl, a heterocycle or a polycycle, and m is zero or an integer in the range of 1 to 8.

While the actual substituents of $C_1$ and $C_2$ can vary widely as necessary for a particular reaction scheme, one important proviso is that at least one substituent of $C_1$ must form a covalent bond with at least one substituent of $C_2$ in order to provide a tetradentate ligand which forms a square complex with M. That is, the ligand is a bridged cycle or polycycle which includes $C_1$ and $C_2$. Furthermore, in order for the catalyst to be chiral, e.g., to be capable of catalyzing stereoselective reactions, $R_1$, $R_2$, $R'_1$, $R'_2$ and other substituents of $C_1$ and $C_2$ are selected to provide at least one stereogenic center or an axis of dissymmetry, e.g. such that the ligand is asymmetric.

In the general structure 100, M represents a transition metal of Group 3–12 or the lanthide series of the periodic table, though preferably a metal ion which is not in its highest oxidation state. In the most preferred embodiments, M will be selected from the group of late transition metals, e.g., from the Group 5–12 metals. Even more preferably, M will be Cr(III). Moreover, the metal can be coordinated with a counteranion or a nucleophile (as in the aged catalyst described below).

Exemplary catalysts of this class are comprised of ligands derived from, for example, salens, porphyrins, crown ethers, azacrown ethers, cyclams, phthalocyanines, and the like.

In a particularly preferred embodiment, the subject reactions use a chiral catalyst having a metal ion complexed via an imine of a chiral ligand, preferably a diimine bridge. Accordingly, such variants of structure 100 can be provided in embodiments wherein any one or more of the Lewis bases is an imine, with metallo-schiff base forms of imines being highly preferred.

To further illustrate, a tetradentate catalyst useful in the subject method can be derived using chiral salen or salen-like ligands (hereinafter "salenates"). The asymmetric metallosalenate catalysts offer a distinct advantage over many other chiral tetradentate catalysts, such as the metalloporphyrinates described infra, in that the salenate ligand can have stereogenic centers located just two bond lengths away from the metal. This proximity of the chiral centers to the reactive site can yield a high degree of stereoselectivity.

As disclosed herein, salen complexes are highly effective catalysts for the enantioselective ring-opening of epoxides and other cyclic compounds with nucleophiles. This reaction is notable not only for its high enantioselectivity and for the utility of its products, but also for its remarkable efficiency as a catalytic process.

Moreover, the synthesis of chiral salenates is well characterized in the art, with more than 150 different chiral metallo salenates having been reported in the literature (see, for review, Collman et al. (1993) *Science* 261:1404–1411). These ligands are easily and inexpensively synthesized on large scale starting from readily available materials, as described in Larrow et al., *J Org Chem* (1994) 59:1939–1942. Importantly, the general familiarity and ease of synthesis of metallosalenates permits the substituents to be readily varied in a systematic fashion in order to adjust the steric or electronic characteristics of the ligand. This feature makes possible the synthesis of ligands which are optimized for particular types of reaction or substrate. It has been found that such steric and electronic "tuning" (described infra) can have significant effects on the yield and e.e. of products formed in asymmetric reactions. In particular, the use of bulky blocking substituents is desirable to achieve high product e.e. in the asymmetric ring opening. Furthermore, the stereogenic moiety can easily be modified to improve enantioselectivity.

In general, the salenate ligands which are useful in the subject method as chiral metallosalenate catalysts can be characterized as two substituted β-iminocarbonyls which are linked to form a tetradentate ligand having at least one stereogenic center. In an exemplary embodiment, a metallosalenate catalyst useful in the asymmetric ring-opening processes of the present invention can be represented by a metal complex with two substituted β-iminocarbonyls having the general formula:

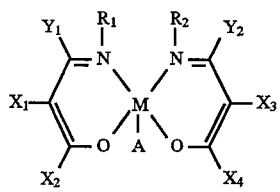

102 in which
the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, or any two or more of the substituents taken together form a carbocycle or heterocycle having from 4 to 8 atoms in the ring structure, which ring structure may be a fused ring, as in the case of, for example, $X_1$ and $X_2$ forming a ring, or which ring may be a bridging ring, as in the case of $R_1$ and $R_2$, $X_2$ and $X_4$, or $Y_1$ and $X_2$ representing different ends of a single substituent, with the proviso that at least one of $R_1$, $Y_1$, $X_1$ and $X_2$ is covalently bonded to at least one of $R_2$, $Y_2$, $X_3$ and $X_4$ to provide the β-iminocarbonyls as a tetradentate ligand;

$R_7$ represents an aryl, a cycloalkyl, a cycloalkenyl, a heterocycle, or a polycycle;

m is zero or an integer in the range of 1 to 8;

M represents a transition metal; and

A represents a counterion or a nucleophile;

wherein each of of the substituents of the β-iminocarbonyls, e.g., $R_1$, $R_2$, $Y_1$, $Y_2$, $X_1$, $X_2$, $X_3$ and $X_4$, are selected such that the catalyst is asymmetric.

The choice of each of $R_1$, $R_2$, $Y_1$, $Y_2$, $X_1$, $X_2$, $X_3$ and $X_4$ is also dependent on electronic and steric considerations, e.g., the tuning of the catalyst for a particular set of substrate and nucleophile, as well as the reactivity of the nucleophile, and the solvent system in which the reaction is to be carried out.

The chirality of the salenate ligand may be the result of the presence of one or more chiral atoms (e.g. carbon, sulfur, phosphorus, or other atoms capable of chirality), or may be the result of an axis of asymmetry due to restricted rotation, helicity, molecular knotting or chiral metal complexation. In preferred embodiments, the chiral ligand has at least one chiral atom or axis of asymmetry due to restricted rotation. Further guidance respecting the particular choice of the substituents is set out herein.

In preferred embodiments, the choice of $R_1$, $R_2$, $X_1$, $X_2$, $X_3$ and $X_4$ yield a class of chiral catalysts which are represented by the general formula

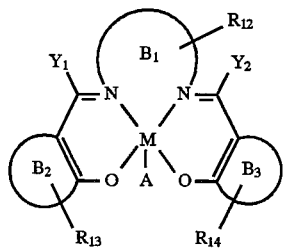

104 in which the $B_1$ moiety represents a diimine bridge, e.g. a bridging substituent which links the imino nitrogens of each β-iminocarbonyl, and preferably contains at least one chiral center of the salen ligand. For example, B1, taken together with the metal-coordinating imines of the β-iminocarbonyl, can represent the diimine of an alkyl, an alkenyl, an alkynyl, or the diimine of —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfur, a sulfonyl, a selenium, or an ester; each of $B_2$ and $B_3$ independently represent rings selected from a group consisting of cycloalkyls, cycloalkenyls, aryls, and heterocycles, which rings comprise from 4 to 8 atoms in a ring structure. The substituents $R_{12}$, $R_{13}$ and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$ (the substituent $R_{12}$ occuring on one or more positions of —$R_{15}$—$R_{16}$—$R_{17}$—). Moreover, any two or more of the $R_{12}$, $R_{13}$, $R_{14}$, $Y_1$ and $Y_2$ substituted taken together can form bridging substituents to bridge the two β-iminocarbonyls and/or bridge different portions of the same β-iminocarbonyl. As above, in order to provide for a chiral catalyst, the choice of $B_2$ and $B_3$ (including their substituents) and/or the choice of substituents on $B_1$ (e.g., $B_1$ has a stereogenic center) is made to establish a chiral ligand. A represents a counteranion or a nucleophile.

In particular, as described in the appended examples, the salenate ligand can be derived from condensation of a substituted salicylaldehyde with a substituted diamine, preferably one stereoisomer of a chiral diamine, and then reacted with a desired metal to form a salen (N,N'-bis (salicylideneamino)alkyl) metal complex. An exemplary reaction for generating the salen ligand is based on Zhang and Jacobsen (1991) *J Org Chem* 56:2296–2298, and Jacobsen et al. PCT WO93/03838, and comprises

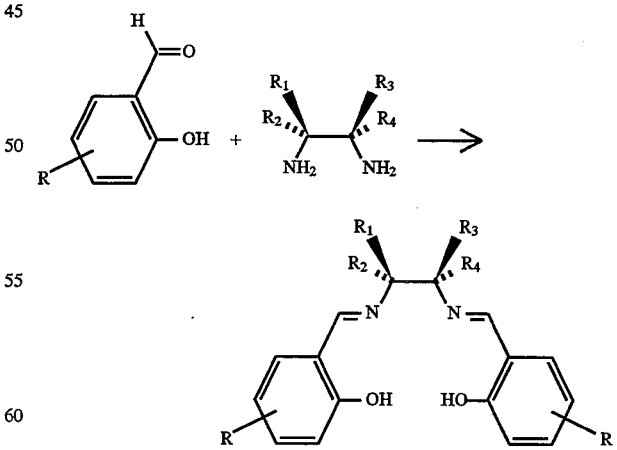

Utilizing this and other reaction schemes generally known in the art can provide a class of salens represented by the general formula:

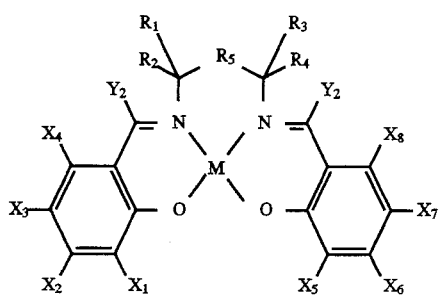

in which
- each of the substituents $R_1, R_2, R_3, R_4, R_5, Y_1, Y_2, X_1, X_2, X_3, X_4, X_5, X_6, X_7,$ and $X_8$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;
- or any two or more of the substituents taken together form a carbocyle or heterocycle having at least 4 atoms in the ring structure;
- $R_7$ represents an aryl, a cycloalkyl, a cycloalkenyl, a heterocycle or a polycycle;
- m is zero or an integer in the range of 1 to 8; and
- M represents a transition metal;

wherein
- if $R_5$ is absent, at least one of $R_1$ and $R_2$ is covalently bonded to at least one of $R_3$ and $R_4$; and the substituents of the salenate ligand are selected such that the salenate has at least one stereogenic center, e.g., is asymmetric. Moreover, the metal can be coordinated with a counterion or a nucleophile (as in the aged catalyst described below).

With respect to generating a chiral ligand, it is important to note when selecting particular substituents that the salenate ligand has a potential catalytic site on both "sides" of the catalyst, e.g., relative to the plane of the four coordinating atoms of the ligand. Accordingly, when selecting the appropriate substituents for the β-iminocarbonyls in the above embodiments, it is important that either (1) both sides of the catalyst have stereogenic centers which effect identical stereoselectivity, or (2) the side having a stereogenic center of appropriate stereoselectivity is accessible while the other side has a blocking structure which substantially impairs approach to the metal atom on that side.

The first of these options is preferred. In other words, it is preferred to have at least one stereogenic center on each side of the salenate ligand, each having the same R/S configuration. For example, (R,R)-1,2-Diphenyl-1,2-bis(3-tert-butylsalicylideamino)ethane, described in Example 1, contains two stereogenic centers on the diimine bridge which give rise to identical stereoselective faces on each side of the catalyst. This bis-faced catalyst has the advantage of not being susceptible to "leakage" reactions because substrate approach, albeit constrained, may occur from either face without loss of selectivity.

In contrast, control of the reactivity of the mono-faced catalyst can be accomplished by sterically hindering substrate approach to the undesired face. For instance, the salenate (R)-2-phenyl-1,2-bis(3-tert-butylsalicylideamino) ethane, e.g., formula 106 wherein $R_1$, $R_2$ and $R_3$ are protons, and $R_4$ is a phenyl, has two non-equivalent faces in terms of enantioselectivity. Accordingly, derivatizing the salenate ligand with a group which blocks access to the "free" face (e.g., the face having both a C1 and C2 proton of the diimine) can establish the ligand as a chiral catalyst with one enantiotopic face. For instance, a "picnic basket" form of the ligand can be generated wherein the phenyl moiety of the diimine bridge is on the "frontside" of the catalyst, and $X_4$ and $X_8$ are covalently linked to form a bridge on the "backside" of the catalyst, which bridge substitution precludes access to the metal ion from the backside. Those skilled in the art will recognize other single- and double-sided embodiments (see, for example, Collman et al. (1993) *Science* 261:1404).

The synthesis schemes for metallosalenates which may be useful in the present method, or precursors thereof, can be adapted from the literature. For example, see Zhang et al. (1990) *J Am Chem Soc* 112:2801; Zhang et al. (1991) *J Org Chem* 56:2296; Jacobsen et al. (1991) *J Am Chem Soc* 113:7063; Jacobsen et al. (1991) *J Am Chem Soc* 113:6703; Lee et al. (1991) *Tetrahedron Lett* 32:5055; Jacobsen, E. N. In *Catalytic Assymetric Synthesis*, Ojima, I., Ed., VCH: New York, 1993, chapter 4.2; E. N. Jacobsen PCT Publications WO81/14694 and WO93/03838; Larrow et al. (1994) *J Am Chem Soc* 116:12129; Larrow et al. (1994) *J Org Chem* 59:1939; Irie et al. (1990) *Tetrahedron Lett* 31:7345; Irie et al. (1991) *Synlett* 265; Irie et al. (1991) *Tetrahedron Lett* 32:1056; Irie et al. (1991) *Tetrahedron Assymetry* 2:481; Katsuki et al. U.S. Pat. No. 5,352,814; Collman et al. (1993) *Science* 261:1404; Sasaki et al. (1994) *Tetrahedron* 50:11827; Palucki et al. (1992) *Tetrahedron Lett* 33:7111; and Srinivasan et al. (1986) *J Am Chem Soc* 108:2309. Exemplary salenate ligands described in the above references are illustrated below, as well as in the appended examples. Ph=phenyl, tBu=t-butyl.

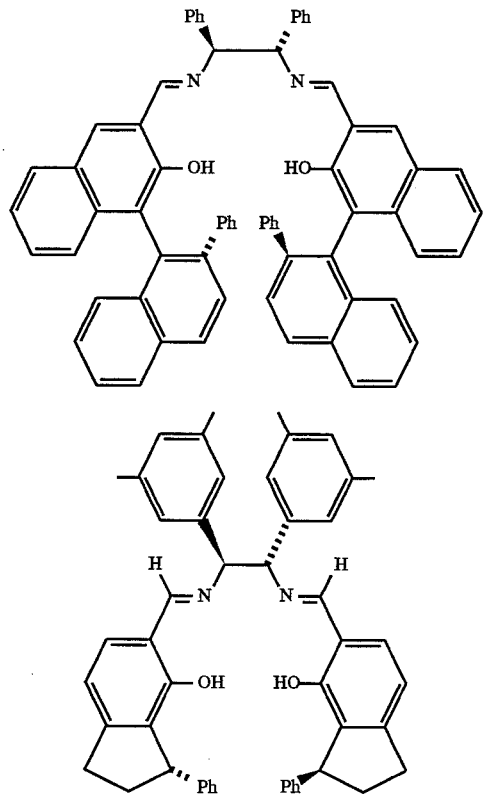

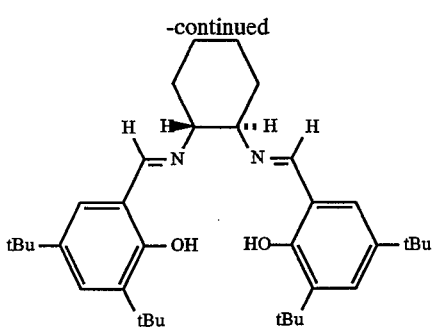

In yet another embodiment of the subject method, the tetradentate catalyst of formula 100 is derived as a chiral tetradentate ligand represented, with the metal atom, by the general formula:

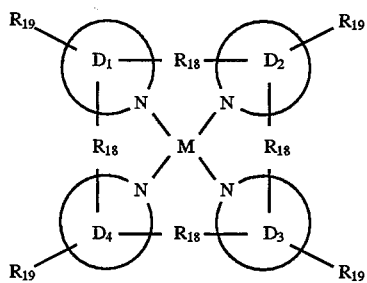

108 in which $D_1$, $D_2$, $D_3$ and $D_4$ each represent heterocycles, such as pyrrole, pyrrolidine, pyridine, piperidine, imidazole, pyrazine, or the like;

each $R_{18}$ occurring in the structure represents a bridging substituent which links adjacent heterocycles, and preferably contains at least one stereogenic center of the ligand. For example, each $R_{18}$, represents an alkyl, an alkenyl, an alkynyl, or —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphonate, a phosphine, a carbonyl, a carboxyl, a silyl, an oxygen, a sulfonyl, a sulfer, a selenium, or an ester;

each $R_{19}$, independently, is absent or represents one or more substituents of the heterocycle to which it is attached, each substituent independently selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, and —$(CH_2)_m$—$R_7$;

or any two or more of the $R_{18}$ and $R_{19}$ substituents are covalently linked to form a bridge substitution;

$R_7$ represents an aryl, a cycloalkyl, a cycloalkenyl, a heterocycle or a polycycle;

m is zero or an integer in the range of 1 to 8; and

M represents a transition metal, wherein each of the substituents $R_{18}$ and $R_{19}$ are selected such that the catalyst is asymmetric, e.g., the catalyst contains at least one stereogenic center. The metal will generally be coordinated with a counteranion or a nucleophile (as in the aged catalyst described below).

In preferred embodiments, $D_1$–$D_4$ are substituted pyrroles, and the catalyst is a chiral porphyrin or porphyrin-like ligand (hereinafter "porphyrinates"). As with the salenate ligands above, the synthesis of a vast number of porphyrinates has been reported in the literature. In general, most chiral porphyrins have been prepared in three ways. The most common approach involves attaching chiral units to preformed porphyrins such as amino- or hydroxy-substituted porphyrin derivatives (Groves et al. (1983) *J Am Chem Soc* 105:5791). Alternatively, chiral substituents can be introduced at the porphyrin-forming stage by allowing chiral aldehydes to condense with pyrrole (O'Malley et al. (1989) *J Am Chem Soc* 111:9116). Chiral porphyrins can also be prepared without the attachment of chiral groups. Similar to the bridged enantiotopic faces described for the salenates above, bridged porphyrinates can be generated by cross-linking adjacent and/or opposite pyrrolic positions and then separating the resulting mono-faced enantiomers with preparative HPLC using a chiral stationary phase (Konishi et al. (1992) *J Am Chem Soc* 114:1313). Ultimately, as with the generation of chiral salenate ligands, the resulting porphyrinate must have no mirror plane in order to be considered chiral.

With reference to formula 100, it will be understood that metalloporphyrinate catalysts, in addition to being represented by formula 108, can be represented generally by the compound of formula 100 when each of $Z_1$, $Z_2$, $Z_3$ and $Z_4$ represent nitrogen, and $C_1$ and $C_2$ along with their substituents (including $R_1$, $R'_1$, $R_2$, $R'_2$) form four substituted pyrrole rings which include $Z_1$, $Z_2$, $Z_3$ and $Z_4$. To complete the square tetradentate ligand, each pyrrole ring is covalently attached to the two adjacent pyrrole rings.

In preferred embodiments, the metalloporphyrinate catalyst is represented by the general formula:

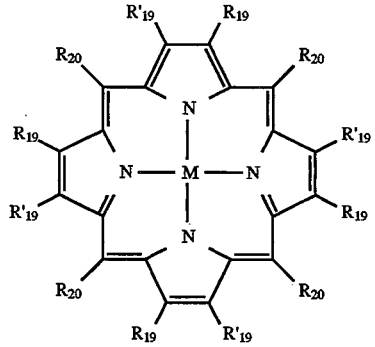

110 in which each $R_{20}$ occurring in structure 110, independently, represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

each $R_{19}$ told $R'_{19}$ occurring in structure 110, independently, represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two $R_{19}$ and $R'_{19}$ substituents on the same pyrrole can be taken together to form a fused carbocycle or fused heterocycle having from 4 to 7 atoms in the ring structure;

or any two or more of the $R_{19}$, $R'_{19}$ and $R_{20}$ substituents are covalently cross-linked to form a bridging substituent;

R₇ represents an aryl, a cycloalkyl, a cycloalkenyl, a heterocycle or a polycycle;

m is zero or an integer in the range of 1 to 8; and

M represents a transition metal, wherein the substituents R₁₉, R'₁₉ and R₂₀ are selected such that the catalyst has at least one stereogenic center, e.g., is asymmetric. The metal will generally be coordinated with a counteranion or a nucleophile (as in the aged catalyst described below).

As with the salenate ligands previously described, it is possible to sterically and electronically "tune" the porphyrin ligands to optimize reaction yield and e.e. Examples of suitable porphyrin ligands and synthesis schemes can be adapted from the art. For example, see Chang et al. (1979) *J Am Chem Soc* 101:3413; Groves et al. (1989) *J Am Chem Soc* 111:8537; Groves et al. (1990) *J Org Chem* 55:3628; Mansuy et al. (1985) *J Chem Soc Chem Commun* p155; Nauta et al. (1991) *J Am Chem Soc* 113:6865; Collman et al. (1993) *J Am Chem Soc* 115:3834; and Kruper et al. (1995) *J Org Chem* 60:725.

Still another class of the tetradentate catalysts represented by the gertreal formula 100 and which are useful in the present asymmetric synthesis reactions can be represented by the formula:

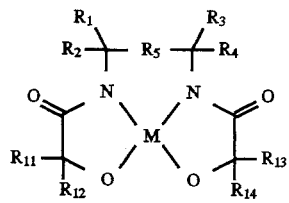

112 in which each of the substituents R₁, R₂, R₃, R₄, R₅, R₁₁, R₁₂, R₁₃ and R₁₄, independently, represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH₂)ₘ—R₇;

or any two or more of the substituents taken together form a carbocycle or heterocycle having at least 4 atoms in the ring structure;

R₇ represents an aryl, a cycloalkyl, a cycloalkenyl, a heterocycle or a polycycle;

m is zero or an integer in the range of 1 to 8; and

M represents a transition metal;

wherein if R₅ is absent, at least one of R₁ and R₂ is covalently bonded to at least one of R₃ and R₄, and the substituents are selected such that the catalyst is asymmetric. The metal will generally be coordinated with a counteranion or a nucleophile (as in the aged catalyst described below).

Exemplary catalysts of formula 112 include:

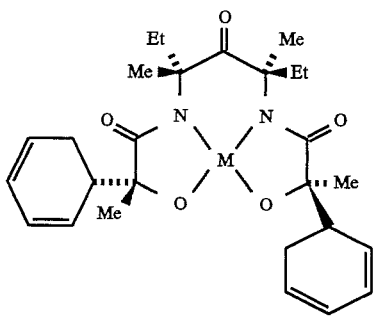

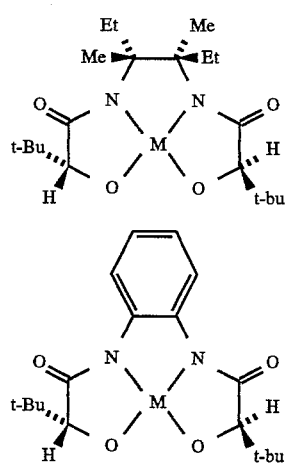

The synthesis of these and other related catalyst can be adapted from the literature. See, for example, Ozaki et al. (1990) *J Chem Soc Perkin Trans* 2:353; Collins et al. (1986) *J Am Chem Soc* 108:2088; and Brewer et al. (1988) *J Am Chem Soc* 110:423.

In yet another embodiment, the tetradentate catalysts of formula 100 can be chosen from the class of azamacrocycle having a ligand represented by the general formula:

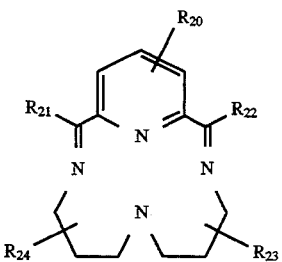

114 wherein

R₂₁ and R₂₂ each represent hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH₂)ₘ—R₇;

R₂₀ is absent or represents one or more substituents of the pyridine to which it is attached, each substituent independently selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH₂)ₘ—R₇;

R₂₃ and R₂₄ each independently are absent or represent one or more substituents of the 1,3-diiminopropyl to which they are attached, each substituent independently selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the $R_{20}$, $R_{21}$, $R_{22}$, $R_{23}$ and $R_{24}$ substituents are covalently linked to form a bridging substituent;

$R_7$ represents an aryl, a cycloalkyl, a cycloalkenyl, a heterocycle or a polycycle; and m is zero or an integer in the range of 1 to 8, wherein the substituents $R_{20}$, $R_{21}$, $R_{22}$, $R_{23}$ and $R_{24}$ are selected such that the catalyst is asymmetric.

One advantage to this class of tetradentate catalysts, like the salenates, derives from the fact that the ligand provides a metallo-shiff base complex. Furthermore, stereogenic centers can be sited within two bond lengths of the metal center. Exemplary ligands of formula 114 include:

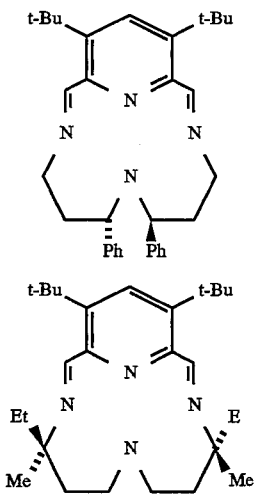

The synthesis of these and other embodiments of 114 are described in Prince et al. (1974) *Inorg Chim Acta* 9:51–54, and references cited therein.

Yet another class of tetradentate ligands of the subject method are the cyclams, such as represented by the general formula:

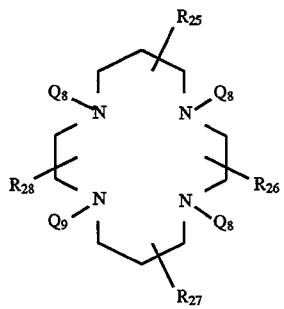

116 in which each of the substituents $Q_8$ indpendently, are absent or represent hydrogen or a lower alkyl, and each of $R_{25}$, $R_{26}$, $R_{27}$ and $R_{28}$, independently, represent one or more substituents on the ethyl or propyl diimine to which they are attached, which substituents are selected from the group of hydrogen, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, and —$(CH_2)_m$—$R_7$; or any two or more of the substituents taken together form a bridging substituent; $R_7$ represents an aryl, a cycloalkyl, a cycloalkenyl, a heterocycle, or a polycycle; and m is zero or an integer in the range of 1 to 8. Wherein the substituents are selected such that the catalyst is asymmetric. Exemplary embodiments and synthesis schemes for chiral cyclams useful in the present invention can be adapted from the art. See, for example, the Burrows et al. U.S. Pat. No. 5,126,464, Kimura et al. (1984) *Inorg Chem* 23:4181; Kimura et al. (1984) *J Am Chem Soc* 106:5497; Kushi et al. (1985) *J Chem Soc Chem Commun* 216; Machida et al. (1986) *Inorg Chem* 25:3461; Kimura et al. (1988) *J Am Chem Soc* 110:3679; and Tabushi et al. (1977) *Tetrahedron Lett* 18:1049

B. Chiral Tridentate Catalysts

In yet another embodiment of the subject method, the chiral catalyst which is provided in the reaction is from a class of chiral catalyst having a tridentate ligand which coordinates a transition metal in a substantially planar geometry, though as above some distortion to this geometry is contemplated. Accordingly, this planar geometry refers to tridentate ligands in which the Lewis basic atoms lie substantially in the same plane, with the metal also in that plane, or slightly above or below that plane.

Preferred planar tridentate catalysts which may be employed in the subject reactions can be represented by the general formula 140:

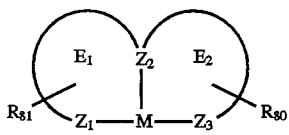

140 wherein $Z_1$, $Z_2$, and $Z_3$ each represent a Lewis base, such as selected from the group consisting of nitrogen, oxygen, phosphorus, arsenic and sulfur; the $E_1$ moiety, taken with $Z_1$, $Z_2$ and M, and the $E_2$ moiety, taken with $Z_2$, $Z_3$ and M, each, independently, form heterocycles; $R_{80}$ and $R_{81}$ each independently are absent, or represent one or more covalent substitutions of $E_1$ and $E_2$ with an organic or inorganic substituent permitted by valence requirements of the ring atom to which it is attached, or any two or more of the $R_{80}$ and $R_{81}$ substituents taken together form a bridging substituent; and M represents a transition metal, wherein each $R_1$, $R_2$, $R'_1$, $R'_2$ $R_{80}$ and $R_8$ substituents are selected to provide at least one stereogenic center in said tridentate ligand. In preferred embodiments, each $R_{80}$ and $R_{81}$ occurring in 140 independently represent hydrogen, halogens, alkyls, alkenyls, alkynyls, hydroxyl, amino, nitro, thiol amines, imines, aides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. The metal will generally be coordinated with a counteranion or a nucleophile (as in the aged catalyst described below).

For example, a chiral tridentate catalyst useful in the subject stereoselective reactions can have a ligand represented by the general formula:

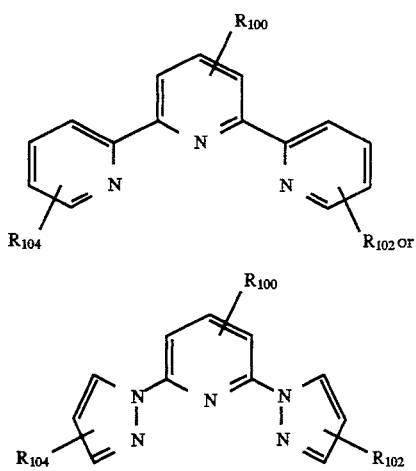

142

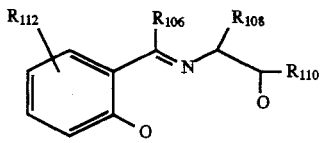

144 wherein each of $R_{100}$, $R_{102}$ and $R_{104}$ each independently are absent, or represent one or more covalent substitutions of heterocycle to which it is attached, or any two or more of the substituents taken together form a bridging substituent; wherein each $R_{100}$, $R_{102}$ and $R_{104}$ substituents, if present, can be selected from the group consisting of halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_7$ represents an aryl, a cycloalkyl, a cycloalkenyl, a heterocycle or a polycycle; and m is zero or an integer in the range of 1 to 8. Again, the substitution of 142 is intended to provide at least one stereogenic center in the tridentate ligand. Exemplary embodiments of the 2,2':6',2''-terpyridine ligands 142 and their synthesis can be adapted from, for example, Potts et al. (1987) *J Am Chem Soc* 109:3961; Hadda et al. (1988) *Polyhedron* 7:575; Potts et al. (1985) *Org Synth* 66:189; and Constable et al. (1988) *Inorg Chim Acta* 141:201. Exemplary 2,6-bis(N-pyrazolyl)pyridine ligands 144 can be adapted from, for example, Steel et al. (1983) *Inorg Chem* 22:1488; and Jameson et al. (1990) *J Org Chem* 55:4992.

Yet another class of planar tridentate catalyst useful in the subject stereoselective reactions can have a ligand represented by the general formula:

146 wherein each of $R_{106}$, $R_{108}$ and $R_{110}$ can be selected from the group consisting of hydrogens, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; $R_{112}$ is absent or represent one or more covalent substitutions of the heterocycle to which it is attached; or any two or more of the $R_{106}$, $R_{108}$, $R_{110}$ and $R_{112}$ substituents taken together form a bridging substituent; $R_7$ represents an aryl, a cycloalkyl, a cycloalkenyl, a heterocycle or a polycycle; and m is zero or an integer in the range of 1 to 8. The choice of substitution of 146 is intended to enhance its chirality. Exemplary embodiments of the salicylaldehyde-derived ligands 146 and their synthesis can be adapted from, for example, Desimoni et al. (1992) *Gazzetta Chimica Italiana* 122:269.

Still another class of planar tridentate catalyst useful in the subject stereoselective reactions can have a ligand represented by the general formula:

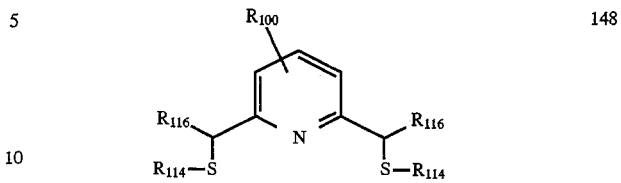

148 wherein $R_{100}$ is as described above, and each $R_{116}$ and $R_{114}$ can be selected from the group consisting of hydrogens, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$; or any two or more of the substituents taken together form a bridging substituent; $R_7$ represents an aryl, a cycloalkyl, a cycloalkenyl, a heterocycle or a polycycle; and m is zero or an integer in the range of 1 to 8. The choice of substitution of 148 is intended to provide at least one stereogenic center in the tridentate ligand. Exemplary embodiments of the salicylaldehyde-derived ligands 148 and their synthesis can be adapted from, for example, Marangoni et al. (1993) *Polyhedron* 12:1669.

C. Tuning the Catalysts

The ligand substituents are chosen to optimize the selectivity of reaction and the catalyst stability. The exact mechanism of action of the metallosalenate-catalyzed ring opening has not yet been precisely elucidated. However, the need for stereoselective nonbonded interactions between the substrate and catalyst is a feature of this and other chiral planar catalysts of the subject reaction which is believed to be comparable to the mechanism of olefin epoxidation by similar catalysts. While not wishing to be bound by any particular theory, it is believed that the present ring opening reactions involve two factors largely responsible for induction of asymmetry by formation of stereospecific nonbonded pairs of catalyst and substrate, namely, steric and electronic interactions between the incoming substrate and the ligand of the chiral catalyst. In general, "tuning" refers altering the steric bulk of the ligand to limit the approach of the substrate, utilizing steric repulsions between the substrate and ligand substituents, and altering the electronic characteristics of the ligand to influence electronic interactions between the substrate and the ligand, as well as the rate and mechanism of the catalyzed reaction. For instance, the choice of appropriate substituents as "blocking groups" enforces certain approach geometries and disfavors others.

Furthermore, the choice of substituent may also affect catalyst stability; in general, builder substituents are found to provide higher catalyst mover numbers. It has been found that for the asymmetric epoxidation of olefins by Mn(salen) complexes, t-butyl groups (or other tertiary groups) are suitable bulky moieties for optimizing stereoselectivity and increasing catalyst mover.

A preferred embodiment for each of the embodiments described above provides a catalyst having a molecular weight less than 10,000 g/m (a.m.u.), more preferably less than 5000 g/m, and even more preferably less than 2500 g/m. In another preferred embodiment, none of the substituents of the core ligand, or any molecule coordinated to the metal in addition to the ligand, have molecular weights in excess 1000 g/m, more preferably they are less than 500 g/m, and even more preferably, are less than 250 g/m. The choice of substituent on the ligand can also be used to influence the solubility of the catalyst in a particular solvent system.

As mentioned briefly above, the choice of ligand substituents can also affect the electronic properties of the catalyst. Substitution of the ligand with electron-rich (electron-donating) moieties (including, for example, alkoxy or amino groups) increases the electron density of the ligand and at the metal center. Conversely, electron-withdrawing moieties (for example, chloro or trifluoromethyl) on the ligand result in lower electron density of the ligand and metal center. The electron density of the ligand is important due to the possibility of interactions (such as pi-stacking) with the substrate (see, e.g., Hamada et al. *Tetrahedron* (1994) 50:11827). The electron density at the metal center may influence the Lewis acidity of the metal or the nucleophilicity of a nucleophile if coordinated to the metal. Choice of appropriate substituents thus makes possible the "tuning" of the reaction rate and the stereoselectivity of the reaction.

Nucleophiles

Nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; 6) It will not substantially react with or degrade the catalyst, e.g. at a rate greater than conversion of the substrate. It will be understood that while undesirable side reactions (such as catalyst degradation) may occur, the rates of such reactions can be manipulated through the selection of reactants and conditions to be slow in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen atom is to be joined to the substrate, a nitrogen nucleophile such as azide, ammonia, phthalimide, hydrazine or an amine may be employed. Similarly, oxygen nucleophiles such as water, hydroxide, alcohols, alkoxides, siloxanes, carboxylates or peroxides may be used to introduce oxygen; and mercaptans, thiolates, bisulfite, thiocyanate and the like may be used to introduce a sulfur-containing moiety. Nucleophiles which introduce other atoms such as halides, selenium, or phosphorus, will be apparent.

In addition, carbon nucleophiles such as cyanide, acetylides, 1,3-dithiane anion, or stabilized carbanions such as enolates may be useful in the present invention.

For any of the above nucleophiles which exist as anions, the counterion can be any of a variety of conventional cations, including alkali and alkaline earth metal cations and ammonium cations. In some cases, nonionic reagents may be useful; for example trimethylsilyl azide (TMS-$N_3$) may be used to deliver the azide nucleophile.

Organometallic reagents such as simple or higher-order organocuprate or organozinc species may also be useful. In certain embodiments, Grignard reagents or organolithium reagents may be employed as nucleophiles.

In certain embodiments, the nucleophile may be part of the substrate, thus resulting in an intramolecular reaction.

In certain embodiments, the nucleophile may be a hydride, by use of, e.g., sodium cyanoborohydride.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain a reactive electrophilic center where a nucleophile may attack. The attack of the nucleophile will cause the breaking of a bond between the electrophilic atom and a leaving group atom, and the formation of a bond between the substrate and the nucleophile. It will further be understood that not all electrophiles will react with every nucleophile.

Most of the cyclic electrophiles contemplated for use in the methods of the present invention contain at least one ring having three to five atoms. Such small rings are frequently strained, making them more susceptible to ring-opening by nucleophiles. However, in some embodiments a cyclic substrate may not be strained, and may have a larger electrophilic ring. Cyclic electrophiles which have good leaving groups (for example, cyclic sulfates) or which have $sp^2$ reactive centers (for example, carbonates or anhydrides) may have electrophilic rings with greater than 5 atoms, for example, from 6 to 9 atoms. Highly activated carbocycles such as certain substituted cyclopropanes (e.g., those substituted with electron-withdrawing groups) also are reactive toward ring-opening with nucleophiles and thus are contemplated for use in the methods of the invention. Furthermore, in certain embodiments it may be desired to use a substrate which has an allylic functionality which may be opened by attack at the allylic double bond in an "$S_N2'$-type" fashion.

Examples of suitable cyclic substrates which can be opened include epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones, and the like.

In certain preferred embodiments, the cyclic substrate will be a meso compound. In other preferred embodiments, the cyclic substrate will be a chiral compound. In certain embodiments, the substrate will be a racemic mixture. In certain embodiments, the substrate will be a mixture of diastereomers.

In exemplary embodiments, a cyclic substrate suitable for use in the present invention has the following formula:

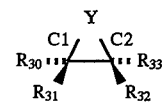

118 in which

Y represents O, S, N($R_{50}$), C($R_{52}$)($R_{54}$), or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group, such as nitro, ketones, aldehydes, sulfonyls, trifluoromethyl, —CN, chloride, and the like; A and C are independently absent, or represent a $C_1$–$C_5$ alkyl, O, S, carbonyl, or N($R_{50}$); and B is a carbonyl, a thiocarbonyl, a phosphoryl, or a sulfonyl;

$R_{30}$, $R_{31}$, $R_{32}$, and $R_{33}$ can be any organic or inorganic substutituent which forms a covalent bond with a carbon atom of 118, and which permits formation of the stable ring structure including Y. For instance, $R_{30}$, $R_{31}$, $R_{32}$, and $R_{33}$ can each independently represent hydrogen, a halogen, an alkyl, an alkenyl, an alkynyl, a hydroxyl, a nitro, a thiol, an amino, an amine, an imine, an amide, a phosphoryl, a phosphonate, a phosphine, a carbonyl, a carboxyl, a silyl, an ether, a thioether, a sulfonyl, a selenoether, a ketone, an aldehyde, an ester, or —$(CH_2)_m$—$R_7$;

or any two or more of the substituents $R_{30}$, $R_{31}$, $R_{32}$, and $R_{33}$ taken together form a carbocylic or heterocyclic ring having from 4 to 8 atoms in the ring structure;

$R_7$ represents an aryl, a cycloalkyl, a cycloalkenyl, a heterocycle or a polycycle; and m is zero or an integer in the range of 1 to 8.

In preferred embodiments, $R_{30}$, $R_{31}$, $R_{32}$, and $R_{33}$ are chosen such that the resulting compound has a plane of symmetry. A leaving group is a functionality which upon bond cleavage departs with an electron pair. In general, good leaving groups are those moieties which are expelled from the substrate as weak bases. For example; sulfates, sulfonates, chloride, bromide, iodide, phosphates and the like are good leaving groups. In addition, some moieties may be good leaving groups when protonated or complexed with a Lewis acid. For example, alkoxide ions are generally poor leaving groups, but alcohols are good leaving groups. It should be noted that ring strain may, in some cases, allow a rather poor leaving group to be expelled, as in the case of epoxides, aziridines, and the like. Though not intended to be limiting, many compounds which have ring strain of more than 20 kcal/mole (compared to cyclohexane) will generally be suitable substrates.

In certain embodiments, the electrophilic atom may be a heteroatom.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the substrate, the catalyst, or the product. For example, the reaction temperature influences the speed of the reaction, as well as the stability of the reactants and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent (see Example 8, infra). Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, ring-opening by the cyanide nucleophile may be performed under an atmosphere of HCN gas. Similarly, in embodiments in which the ring-expansion of an epoxide by carbon dioxide or a similar reaction is desired, the reaction may be performed under an atmosphere of carbon dioxide, or a mixture of carbon dioxide and other gases. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, derivativation with one or more of substituents of the ligand. The immobilized ligands can be complexed with the desired metal to form the chiral metallocatalyst. The catalyst, particularly the "aged" catalyst described herein (Example 8, infra), is easily recovered after the reaction as, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

EXAMPLE 1

Preparation of (R,R)-1,2-Diphenyl-1,2-bis(3-tert-butylsalicylideamino)ethane

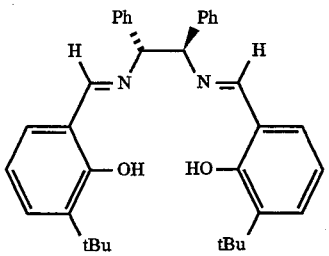

A solution of 360.5 mg (2.0 mmol) of 3-tert-butylsalicylaldehyde in 3 ml of EtOH was added dropwise to a solution of 212.3 mg (1.0 mmol) of (R,R)-1,2-diamino-1,2-diphenylethane in 5 ml of EtOH. The reaction mixture was heated to reflux for 1 h and water (5 ml) was added. The oil that separated solidified upon standing. Reerystallization from MeOH/H$_2$O gave 485.8 mg (91%) of yellow powder, mp 73°–74° C. $^1$H NMR (CDCl$_3$) δ 1.42 (s, 18H, CH$_3$), 4.72 (s, 2H, CHN=C), 6.67–7.27 (m, 16H, ArH), 8.35 (s, 2H, CH=N), 13.79 (s, 2H, ArOH) ppm; $^{13}$C NMR (CDCl$_3$) δ 29.3, 34.8, 80.1, 117.8, 118.5, 127.5, 128.0, 128.3, 129.6, 130.1, 137.1, 139.5, 160.2, 166.8 ppm. Anal. Calcd. for C$_{36}$H$_{40}$N$_2$O$_2$. C, 81.17; H, 7.57; N, 5.26. Found: C, 81.17; H, 7.60; N, 5.25.

EXAMPLE 2

Preparation of (R,R)-1,2-Diphenyl-1,2-bis(3-diphenylmethylsilylsalicylideamino)ethane

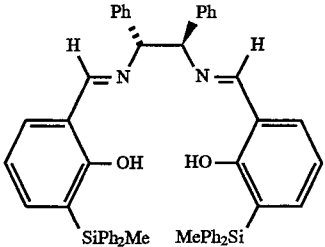

3-(Diphenylmethylsilyl)salicylaldehyde was prepared from 2-bromophenol in 5 steps according to established procedures. A solution of 348.3 mg (1.09 mmol) of 3-(diphenylmethylsilyl)salicylaldehyde and 116.0 mg (0.546 mmol) of (R,R)-1,2-diamino-1,2-diphenylethane in 5 ml of ethanol was heated to reflux for 0.5 h. A bright yellow oil separated from the solution and it solidified upon standing. The mixture was filtered and the yellow solid was washed with 2×5 ml ethanol. The isolated yield of product pure by $^1$H NMR analysis was 416 mg (97%). $^1$H NMR (CDCl$_3$) δ 0.95 (s, 3H), 4.68 (s, 2H), 6.72–7.55 (m, 36H, ArH), 8.37 (s, 2H), 13.34 (s, 2H) ppm.

EXAMPLE 3

Preparation of 2,2'-Bis(3-tert-Butylsalicylideamino)-1,1'-Binaphthyl.

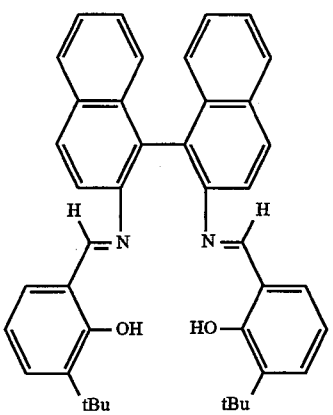

A solution of 725 mg (4.0 mmol) of 3-tert-butylsalicylaldehyde in 6 ml of EtOH was added dropwise to a solution of 569 mg (2.0 mmol) of (+)-2,2'-diamino-1,1'-binaphthyl in 5 ml of EtOH. The reaction mixture was heated to reflux for 8 h and then volatile materials were removed under vacuum. The residue was purified by flash chromatography on 80 g SiO$_2$, using 20% CH$_2$Cl$_2$ in hexane as eluent. The mobile yellow fraction was collected and solvents were removed under vacuum to give 725 mg (1.20 mmol, 59% yield) of the diimine as a yellow powder.

EXAMPLE 4

Preparation of (S,S)-1,2,-bis(3,5-di-tert-butylsalicylide-amino)cyclohexane (2)

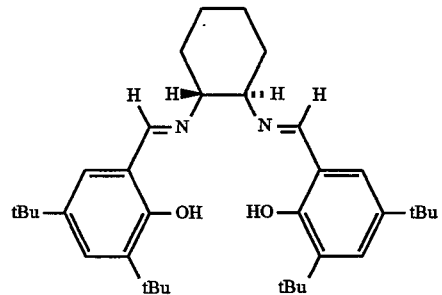

3,5-Di-t-butylsalicylaldehyde (2.0 equivalents) (prepared from the inexpensive, commercially available 2,4-di-t-butylphenol according to Larrow, J. F.; Jacobsen, E. N.; Gao, Y.; Hong, Y.; Nie, X.; Zepp, C. M. *J Org Chem* 1994, 59, 1939) was added as a solid to a 0.2M solution of (S,S)-1, 2-diaminocyclohexane (1.0 equivalent) (Aldrich Chemical Co., Milwaukee, Wis.) in absolute ethanol. The mixture was heated to reflux for 1 hr. and then H$_2$O was added dropwise to the cooled bright yellow solution. The resulting yellow crystalline solid was collected by filtration and washed with a small portion of 95% ethanol. The yield of analytically pure salen ligand 2 obtained in this manner was 90–97%.

Spectroscopic and analytical data for the salen ligand: $^1$H NMR (CDCl$_3$) δ 13.72 (s, 1H), 8.30 (S, 1H), 7.30 (d, J=2.3 Hz, 1H), 6.98 (d, J=2.3 Hz, 1H), 3.32 (m, 1H), 2.0–1.8 (m, 2H), 1.8–1.65 (m, 1H), 1.45 (m, 1H), 1.41 (s, 9H), 1.24 (s, 9H). $^{13}$C NMR (CDCl$_3$): δ 165.8, 158.0, 139.8, 136.3, 126.0, 117.8, 72.4, 34.9, 33.0, 31.4, 29.4, 24.3. Anal. Calcd. for $C_{36}H_{54}N_2O_2$: C, 79.07; H, 9.95; N, 5.12. Found: C, 79.12; H, 9.97; N, 5.12.

EXAMPLE 5

Preparation of (R,R)- and (S,S)-[1,2-bis(3,5-di-tert-butylsalicylideamino)cyclohexane]-manganese(III) chloride.

The salen ligand synthesized in Example 4 is redissolved in hot absolute ethanol to give a 0.1M solution. Solid Mn(OAc)$_2$•4H$_2$O(2.5 equivalents) is added in one portion and the solution is refluxed for 1 hr. Approximately 5 equivalents of solid LiCl are then added and the mixture is heated to reflux for an additional 0.5 hr. Cooling the mixture to 0° C. and addition of a volume of water equal to the volume of the brown ethanolic solution affords the Mn(III) complex as a dark brown powder which is washed thoroughly with H$_2$O, and isolated by filtration in 81–93% yield. Acceptable C, H, N, Cl and Mn analyses of the catalyst have been obtained (±0.4%), but these vary according to the extent of water and ethanol incorporation in the powdery product. The solvent content of the catalyst does not influence its effectiveness.

Analytical data for this catalyst: Anal. Calcd for $C_{36}H_{52}ClMnN_2O_2$•$C_2H_5OH$: C, 67.19; H, 8.31; Cl, 5.22; Mn, 8.09; N, 4.12: Observed: C, 67.05; H, 8.34; Cl, 5.48; Mn, 8.31; N, 4.28.

EXAMPLE 6

Preparation of (R,R)-[1,2-bis(3,5-di-tert-butylsalicylideamino)cyclohexane]-chromium(III) chloride (1)

The following procedure was found to provide 1 with reproducible catalytic activity. Under a nitrogen atmosphere, 0.309 g (2.52 mmol) of CrCl$_2$ (anhydrous, 99.9%, Alfa/Johnson Matthey) was added to the (R,R)-ligand 2 synthesized in Example 4 (1.25 g, 2.29 mmol) in dry, degassed THF (45 mL). The resulting dark brown solution was stirred under N$_2$ for 3 h and then in air for an additional 3 h. The solution was then diluted with 250 ml of t-butyl methyl ether and washed with satd. NH$_4$Cl (3×150 ml) and brine (3×150 ml). The organic phase was dried (Na$_2$SO$_4$) and solvent was removed under reduced pressure, affording 1.41 g (87% yield) of 1 as a brown solid which was >98% pure as determined by HPLC analysis (octadecyl reverse phase, 100% CH$_3$CN). This material was used in the ring opening reactions without further purification. Recrystallization from acetonitrile provided high quality orange-brown crystals with 63% recovery: mp 375°–398° C. (dec). IR (KBr, cm$^{-1}$) 3610 (br), 3420 (br), 2951(s), 2866, 1619(s), 1531, 1434, 1390, 1321, 1255, 1170, 1030, 837, 785, 748, 563, 543. Anal. Calcd for $C_{38}H_{59}N_2O_4CrCl$ 1•3/2H$_2$O•1/2THF: C, 65.64; H, 8.55; N, 4.03; Cr, 7.48; Cl, 5.10. Found: C, 65.72; H, 8.53; N, 4.04; Cr, 7.45; Cl, 5.15. MS (FD): m/z 631 ([M]+). HRMS (FAB): m/z calcd for [$C_{36}H_{52}N_2O_2Cr$]+ ([1–Cl 596.3418, found 596.3434. $\mu_{eff}$=3.97 $\mu_B$.

Conductance (CH$_3$CN, 0.0045M) 0.57 $\Omega^{-1}$ cm$^2$ mol$^{-1}$.

EXAMPLE 7

Ring-opening of meso-epoxides catalyzed by Cr (salen) complexes

Metal complexes of the readily available chiral salen ligand 2 were screened as catalysts for the model reaction of cyclohexene oxide with TMS-N$_3$. Complexes of Al, Ti, and Mn each catalyzed the reaction, but the azido silylether product 4 was generated in racemic form. In contrast, the corresponding Cr complex 1 catalyzed ring-opening to generate 4 with up to >80% ee. In addition, trace amounts of the byproducts 5 and 6 were observed, in molar concentrations similar to the concentration of catalyst (2 mol %). The reaction could be carried out under a variety of reaction conditions and in a wide range of solvents, however highest enantioselectivities were obtained using ethereal solvents (t-butyl methyl ether, THF, Et$_2$O).

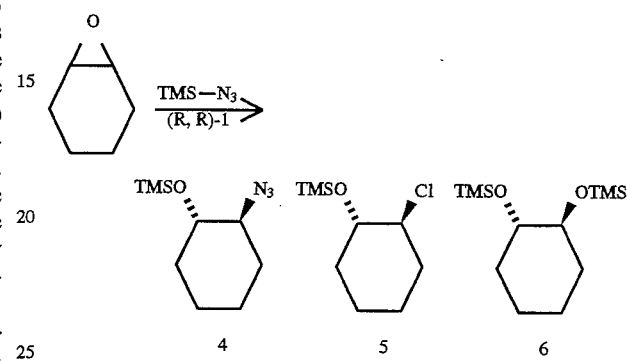

The reaction of a variety of meso epoxides with Me$_3$SiN$_3$ was screened with catalyst 1 (Table I) according the following general procedure:

A 5 mL flask is charged with 42 mg (0.060 mmol) of 1 and 1.0 mL of Et$_2$O. The epoxide (3.00 mmol) is added and the mixture is stirred for 15 min, at which time Me$_3$SiN$_3$ (0.418 mL, 3.15 mmol) is added. The resulting brown solution is stirred at room temperature for the indicated time (Table I). The solution is then concentrated in vacuo and the residue is filtered through a 10 mL plug of silica gel with 100 mL of 5–20% EtOAc/hexanes. The filtrate is concentrated and the resulting residue is subjected to analysis by GC or HPLC to determine the enantiomeric composition of silylated azidoalcohol.

Desilylation: The product obtained as described above is dissolved in methanol (5 mL). (1S)-(+)-10-Camphorsulfonic acid (35 mg, 0.15 mmol) is added and the resulting solution is stirred for 30 min and then concentrated in vacuo. The residue is purified by flash chromatography to afford pure azidoalcohol.

Five-membered ring epoxides underwent ring-opening with very high levels of enantioselectivity, while 6-membered ring and acyclic epoxides afforded somewhat diminished selectivities. Ether, olefin, and carbonyl-containing functional groups were all tolerated (entries 2–4,7). Interestingly, 3,4-epoxytetrahydrofuran (entry 2) was one of the most reactive epoxides in this study, suggesting that Lewis bases do not inhibit catalytic activity.

TABLE I

Enantioselective opening of meso epoxides with 1.[a]

$$\underset{R}{\overset{R}{\diagup}}\!\!\!\diagdown\!\!\!\text{O} + \text{Me}_3\text{SiN}_3 \xrightarrow[\text{2. CSA, MeOH}]{\text{1. 1 (2 mol \%)Et}_2\text{O}} \underset{R}{\overset{R}{\diagup}}\!\!\!\overset{N_3}{\diagdown}\!\!\!\text{OH}$$

| entry | epoxide | time (h) | Isolated yield (%)[b] | ee(%)[c] |
|---|---|---|---|---|
| 1 | cyclopentene oxide | 28 | 80 | 94 |
| 2 | 3,4-epoxytetrahydrofuran | 18 | 80 | 98 |
| 3 | Fmoc-N pyrroline oxide | 36 | 80 | 95 |
| 4 | F₃C-C(O)-N pyrroline oxide | 16 | 90 | 95 |
| 5 | 3-oxo cyclopentene oxide | 14 | 65 | 88 |
| 6 | cyclohexene oxide | 18 | 80 | 88 |
| 7 | 1,4-cyclohexadiene monoepoxide | 46 | 72 | 81 |
| 8 | 2,3-dimethyl-2,3-epoxybutane | 30 | 65[d] | 82 |

[a]All reactions were run on 3.0 mmol scale of epoxide. Absolute configurations for the products from entries 1, 6 and 8 were determined as in H. Yamashita Bull Chem Soc Jpn (1988) 61:1213. The absolute configurations of the remaining products were assigned by analogy.
[b]Isolated yield of azidoalcohol, unless noted otherwise.
[c]All ee's were determined by chiral chromatography.
[d]Isolated yield of the trimethylsilylether.

EXAMPLE 8

Solvent-free enantioselective ring-opening reactions

The enantioselectivity of the epoxide ring-opening reaction was found to be remarkably insensitive to the initial concentration of reagents. We therefore investigated solvent-free reactions in which, in principle, no reaction byproducts of any kind are generated (Table II). Thus, reaction of 5 mmol of cyclohexene oxide with 2 mol % catalyst 1 and 5.25 mmol (1.05 equiv) of TMSN₃ for 18 h, followed by short path distillation under reduced pressure, afforded an 86% yield of the TMS-protected azido alcohol in 84% e.e. (cycle 1). As expected, this product was contaminated with small amounts of (≦2% of each) of silylated chlorohydrin 5 and bis-silylated diol 6. Treatment of the residual catalyst with additional portions of cyclohexene oxide (5 mmol) and TMSN₃(5.25 mmol) resulted in an 88% yield of product (87% ee) that was completely free of any byproducts (cycle 2). An additional recycling of the catalyst gave the product in 91% yield and 88% ee (cycle 3). A fourth reaction was then performed with cyclopentene oxide and the corresponding product was obtained in 81% yield and 94% ee (cycle 4). Finally, 1,4-cyclohexadiene monoepoxide was used for the fifth cycle (75% yield, 83% ee; cycle 5). In all cases, complete conversion of the epoxide was observed at the times indicated.

TABLE II

Solvent-Free enantioselective Opening of Meso Epoxides with Trimethylsilylazide and Recycled Catalyst (R,R)-1[a]

$$\underset{R}{\overset{R}{\diagup}}\!\!\!\diagdown\!\!\!\text{O} \xrightarrow[\text{2. Distillation}]{\text{1. 2 mol \% Cat., TMSN}_3} \underset{R}{\overset{R}{\diagup}}\!\!\!\overset{N_3}{\diagdown}\!\!\!\text{OTMS}$$

| entry | epoxide | time (h) | Isolated yield (%)[b] | ee(%)[c] |
|---|---|---|---|---|
| 1 | cyclohexene oxide | 18 | 86 | 84 |
| 2 | cyclohexene oxide | 21 | 88 | 87 |
| 3 | cyclohexene oxide | 20 | 91 | 88 |
| 4 | cyclopentene oxide | 4 | 81 | 94 |
| 5 | 1,4-cyclohexadiene monoepoxide | 18 | 75 | 83 |

[a]All cycles were run with 5.00 μmol of epoxide and 5.25 mmol of TMSN₃
[b]Isolated yield of distilled TMS protected azidoalcohol.
[c]Determined by chiral GC.

Based on these results, the first reaction can be thought of as an "aging" of the catalyst. Consistent with the observation of silylated chlorohydrin 5 in the first reaction only, the "aged" catalyst contains no chlorine as judged by elemental analysis. This catalyst also displays an absorbance at 2058 cm⁻¹ in its infrared spectrum, consistent with a Cr—N₃ N=N stretch. We therefore conclude that the active catalyst is (salen) Cr—N₃. While not wishing to be bound by any particular theory, it appears that catalysis involves Lewis acid activation by the chromium center or nucleophilic delivery of azide by a Cr—N₃ intermediate, or both. The apparent intermediacy of a Cr—N₃ intermediate provides circumstantial support for the latter.

EXAMPLE 9

Kinetic resolution of chiral racemic epoxides

We have also investigated the use of catalyst 1 for the kinetic resolution of chiral racemic epoxides. Preliminary results are shown in Table III. Thus, treatment of 3 mmol of styrene oxide with 0.70 equiv. of TMSN₃ and 2 mol % of catalyst 1 resulted in 76% conversion (based on the available enantiomer) of the epoxide to a complex mixture of products. The ee of the unreacted styrene oxide was 98%. Similarly, epichlorohydrin proceeded to 80% conversion (based on the available enantiomer) when treated with 0.60 equiv of $TMSN_3$ and 2 mol % 1. The ee of the unreacted epichlorohydrin was 97%.

TABLE III

Trimethylsilylazide Catalyzed by (R,R)-1[a]

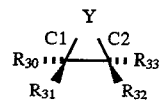

| epoxide | equiv $TMSN_3$ | time (h) | conv. (%)[b] | ee(%)[c] |
|---|---|---|---|---|
| (phenyl epoxide) | 0.70 | 67 | 76 | 98 (R) |
| (chloromethyl epoxide) | 0.60 | 21 | 80 | 98 (R) |

[a]All reactions were with 3.00 mmol of epoxide, 0.060 mmol catalyst and the indicated amount of $TMSN_3$ in 1.0 mL $Et_2O$
[b]Determined by GC employing nonane as internal standard.
[c]Determinned by chiral GC.

EXAMPLE 10

Synthesis of a chiral porphyrin ligand

Pyrrole (1.0 equivalents) and salicylaldehyde (1.2 equivalents) are dissolved in propionic acid (1 liter/20 ml pyrrole) and the solution is refluxed for 30 minutes. The reaction mixture is allowed to cool to room temperature and stand for one day. The mixture is filtered and the product is recrystallized to yield 5,10,15,20-tetrakis(2'-hydroxyphenyl)porphyrin.

The above-named porphyrin is dissolved in dimethylformamide, cooled to 0° C., and treated with sodium hydride (4 equivalents). The mixture is stirred for 30 minutes, and then a solution of D-threitol 1,4-ditosylate (Aldrich Chemical Co.) in DMF is added slowly. When the addition is finished, the reaction mixture is stirred for 30 minutes more, then carefully quenched. The organic phase is washed with brine and the solvent is evaporated. The residue is purified by HPLC to yield the chiral porphyrin.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A process of stereoselective chemical synthesis which comprises reacting a nucleophile and a chiral or prochiral cyclic substrate in the presence of a non-racemic chiral catalyst to produce a stereoisomerically enriched product, wherein said cyclic substrate comprises a carbocycle or heterocycle having a reactive center susceptible to nucleophilic attack by said nucleophile, and said chiral catalyst comprises an asymmetric tetradentate ligand complexed with a metal atom, which complex has a rectangular planar or rectangular pyramidal geometry.

2. The process of claim 1, wherein the metal atom is a transition metal from Groups 3–12 or from the lanthanide series.

3. The process of claim 1, wherein the metal atom is a late transition metal which is not in its highest state of oxidation.

4. The process of claim 2, wherein the metal atom is selected from the group consisting of Cr, Mn, V, Fe, Mo, W, Ru and Ni.

5. The process of claim 1, wherein the tetradentate ligand is selected from the group consisting of a chiral ligand represented by the formula 102, a chiral ligand represented by the formula 108, a chiral ligand represented by the formula 112, a chiral ligand represented by the formula 114, a chiral ligand represented by the formula 116, and a chiral crown ether.

6. The process of claim 1, wherein the tetradentate ligand has at least one schiff base complexes with the metal atom.

7. The process of claim 1, wherein the chiral catalyst has a molecular weight of less than 10,000 a.m.u.

8. The process of claim 1, wherein the substrate is represented by the general formula 118:

$$\begin{array}{c} Y \\ C1 \diagdown C2 \\ R_{30}\cdots \diagup \diagdown \cdots R_{33} \\ R_{31} \quad R_{32} \end{array} \quad 118$$

in which

Y represents O, S, $N(R_{50})$, $C(R_{52})(R_{54})$, or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or $N(R_{50})$; and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y.

9. The process of claim 8, wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

or any two or more of the substituents $R_{30}$, $R_{31}$, $R_{32}$, and $R_{33}$ taken together form a carbocylic or heterocyclic ring having from 4 to 8 atoms in the ring structure; $R_7$ represents an aryl, a cycloalkyl, a cycloalkenyl, a heterocycle or a polycycle; and m is zero or an integer in the range of 1 to 8.

10. The process of claim 8, wherein $R_{30}$, $R_{31}$, $R_{32}$, and $R_{33}$ are chosen such that the substrate has a plane of symmetry.

11. The process of claim 1, wherein the cyclic substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

12. The process of claim 1, wherein the catalyst is immobilized on an insoluble matrix.

13. The process of claim 1, which process is an enantioselective reaction.

14. The process of claim 1, which process is a diastereoselective reaction.

15. The process of claim 14, which diastereoselective reaction is a kinetic resolution reaction.

16. A process of stereoselective chemical synthesis which comprises reacting a nucleophile and a chiral or prochiral cyclic substrate in the presence of a non-racemic chiral catalyst to produce a stereoisomerically enriched product, wherein said cyclic substrate comprises a carbocycle or heterocycle having a reactive center susceptible to nucleophilic attack by said nucleophile, and said chiral catalyst comprises an asymmetric tridentate ligand complexed with a metal atom, which complex has a planar geometry.

17. A stereoselective ring opening process which comprises combining a nucleophilic reactant, a prochiral or chiral cyclic substrate, and a non-racemic chiral catalyst, wherein said cyclic substrate comprises a carbocycle or heterocycle having an electrophilic atom susceptible to attack by said nucleophile, and said chiral catalyst comprises a chiral ligand having at least one schiff base nitrogen complexed with a late-transition metal which is not in its highest state of oxidation; and maintaining the combination under conditions appropriate for said chiral catalyst to catalyze stereoselective opening of said cyclic substrate at said electrophilic atom by reaction with said nucleophilic reactant.

18. The process of claim 17, wherein the metal is a selected from Group 5–12 transition metals.

19. The process of claim 17, wherein the metal is a Group 6 transition metal.

20. The process of claim 17, wherein the metal atom is selected from the group consisting of Cr, Mn, V, Fe, Mo, W, Ru and Ni.

21. The process of claim 17, wherein the catalyst comprises a tetradentate ligand.

22. The process of claim 21, wherein the catalyst is represented by the general formula:

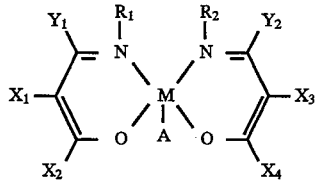

in which the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, or any two or more of the substituents taken together form a carbocyle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, and at least one of $Y_1$ and $Y_2$ is a hydrogen;

$R_7$ represents an aryl, a cycloalkyl, a cycloalkenyl, a heterocycle, or a polycycle;

m is zero or an integer in the range of 1 to 8;

M represents the late transition metal; and

A represents a counterion or a nucleophile, wherein each of of the substituents $R_1$, $R_2$, $Y_1$, $Y_2$, $X_1$, $X_2$, $X_3$ and $X_4$, are selected such that the catalyst is asymmetric.

23. The process of claim 17, wherein the catalyst comprises a tridentate ligand.

24. The process of claim 17, wherein the substrate is represented by the general formula:

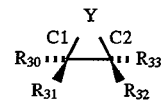

in which

Y represents O, S, $N(R_{50})$, $C(R_{52})(R_{54})$, or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or $N(R_{50})$; and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y.

25. The process of claim 24, wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents $R_{30}$, $R_{31}$, $R_{32}$, and $R_{33}$ taken together form a carbocyle or heterocycle having from 4 to 8 atoms in the ring structure;

$R_7$ represents an aryl, a cycloalkyl, a cycloalkenyl, a heterocycle or a polycycle; and m is zero or an integer in the range of 1 to 8.

26. The process of claim 24, wherein $R_{30}$, $R_{31}$, $R_{32}$, and $R_{33}$ are chosen such that the substrate has a plane of symmetry.

27. The process of claim 17, wherein the cyclic substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

28. The process of claim 17, which process is an enantioselective ring opening.

29. The process of claim 17, which process is a diastereoselective ring opening.

30. The process of claim 29, which diastereoselective ring opening produces a kinetic resolution.

31. The process of claim 17, wherein the chiral catalyst has a molecular weight of less than 10,000 a.m.u.

32. A method for catalyzing a stereoselective ring opening reaction which comprises combining a nucleophile, a prochiral or chiral cyclic substrate, and a non-racemic chiral catalyst, wherein said cyclic substrate comprises a carbocycle or heterocycle having an reactive center susceptible to attack by said nucleophile, and said chiral catalyst comprises a chiral tetradentate ligand complexed with a late-transition metal which is not in its highest state of oxidation; and maintaining the combination under conditions appropriate for said chiral catalyst to catalyze stereoselective opening of said cyclic substrate at said reactive center by nucleophilic attack by the said nucleophile.

33. The method of claim 32, wherein the chiral catalyst is represented by the general formula:

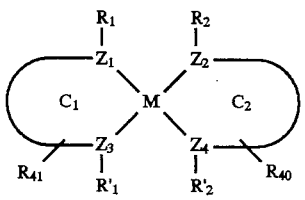

100 in which $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents the late transition metal; and

A represents a counterion or a nucleophile, wherein each $R_1$, $R_2$, $R'_1$, $R'_2$ $R_{40}$ and $R_{41}$ are selected to provide at least one stereogenic center in said tetradentate ligand.

34. The method of claim 33, wherein $R_1$, $R_2$, $R'_1$ and $R'_2$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

each $R_{40}$ and $R_{41}$ occuring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

$R_7$ represents an aryl, a cycloalkyl, a cycloalkenyl, a heterocycle or a polycycle; and m is zero or an integer in the range of 1 to 8.

35. The method of claim 33, wherein each $Z_1$, $Z_2$, $Z_3$ and $Z_4$ are independently selected from the group consisting of nitrogen, oxygen, phosphorus, arsenic, and sulfur.

36. The method of claim 33, wherein the M represents a late transition metal from one of the Group 5-12 transition metals.

37. The method of claim 32, wherein the metal atom is selected from the group consisting of Cr, Mn, V, Fe, Mo, W, Ru and Ni.

38. The method of claim 33, wherein the M is Group 6 transition metal.

39. The method of claim 38, wherein the M is Cr(III).

40. The method of claim 32, wherein the tetradentate ligand is selected from the group consisting of a chiral ligand represented by the formula 102, a chiral ligand represented by the formula 108, a chiral ligand represented by the formula 112, a chiral ligand represented by the formula 114, and a chiral ligand represented by the formula 116.

41. The method of claim 32, wherein the substrate is represented by the general formula:

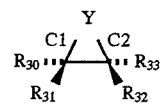

118 in which

Y represents O, S, N($R_{50}$), C($R_{52}$)($R_{54}$), or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$-$C_5$ alkyl, O, S, carbonyl, or N($R_{50}$); and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y.

42. The method of claim 41, wherein the substituents wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

or any two or more of the substituents $R_{30}$, $R_{31}$, $R_{32}$, and $R_{33}$ taken together form a carbocycle or heterocycle having from 4 to 8 atoms in the ring structure;

$R_7$ represents an aryl, a cycloalkyl, a cycloalkenyl, a heterocycle or a polycycle; and m is zero or an integer in the range of 1 to 8.

43. The method of claim 41, wherein $R_{30}$, $R_{31}$, $R_{32}$, and $R_{33}$ are chosen such that the substrate has a plane of symmetry.

44. The method of claim 41, wherein the substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

45. The method of claim 27, which process is an enantioselective ring opening.

46. The method of claim 27, which process is a diastereoselective ring opening.

47. The method of claim 46, which diastereoselective ring opening produces a kinetic resolution.

48. A method for catalyzing a stereoselective ring opening reaction which comprises combining a nucleophile, a prochiral or chiral cyclic substrate, and a non-racemic chiral catalyst, wherein said cyclic substrate comprises a carbocycle or heterocycle having an reactive center susceptible to attack by said nucleophile, and said chiral catalyst comprises a chiral tridentate ligand complexed with a late-transition metal which is not in its highest state of oxidation; and maintaining the combination under conditions appropriate for said chiral catalyst to catalyze stereoselective opening of said cyclic substrate at said reactive center by nucleophilic attack by the said nucleophile.

49. The method of claim 48, wherein the chiral tridentate ligand of the chiral catalyst is represented by the general formula:

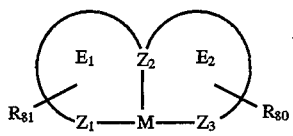

140 in which $Z_1$, $Z_2$, and $Z_3$ each represent a Lewis base;

the $E_1$ moiety, taken with $Z_1$, $Z_2$ and M, and the $E_2$ moiety, taken with $Z_2$, $Z_3$ and M, each, independently, form a heterocycle;

$R_{80}$ and $R_{81}$ each independently are absent, hydrogen, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, or any two or more of the $R_{80}$ and $R_{81}$ substituents taken together form a bridging substituent;

$R_7$ represents an aryl, a cycloalkyl, a cycloalkenyl, a heterocycle or a polycycle;

m is zero or an integer in the range of 1 to 8;

M represents a transition metal; and

A represents a counteranion or a nucleophile, wherein the tridentate ligand is asymmetric.

50. A method for synthesis of enantiomerically enriched chiral compounds, comprising reacting a nucleophile with a prochiral or chiral cyclic substrate in the presence of a chiral catalyst, and under conditions which said chiral catalyst catalyzes enantioselective opening of said cyclic substrate by nucleophilic attack of the cyclic substrate by the nucleophile to produce a product which is enantiomerically enriched relative to a racemic mixture produced in the absence of said chiral catalyst, wherein the chiral cyclic substrate is represented by the general formula:

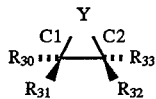

118 in which

Y represents O, S, $N(R_{50})$, $C(R_{52})(R_{54})$, or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or $N(R_{50})$; and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y; and the chiral catalyst is represented by the general formula:

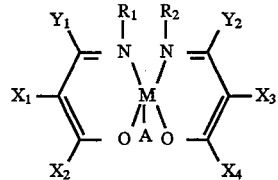

the substituents $R_1$, $R_2$, $Y_1$, $Y_2$, $X_1$, $X_2$, $X_3$ and $X_4$ each, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$, or any two or more of the substituents taken together form a carbocyle or heterocycle ring having from 4 to 8 atoms in the ring structure, with the proviso that at least one of $R_1$, $Y_1$, $X_1$ and $X_2$ is covalently bonded to at least one of $R_2$, $Y_2$, $X_3$ and $X_4$ to provide the β-iminocarbonyls to which they are attached as a tetradentate ligand, and at least one of $Y_1$ and $Y_2$ is a hydrogen;

$R_7$ represents an aryl, a cycloalkyl, a cycloalkenyl, a heterocycle, or a polycycle;

m is zero or an integer in the range of 1 to 8;

M represents the late transition metal; and

A represents a counterion or a nucleophile, wherein each of of the substituents $R_1$, $R_2$, $Y_1$, $Y_2$, $X_1$, $X_2$, $X_3$ and $X_4$, are selected such that the catalyst is asymmetric.

51. The method of claim 50, wherein the M represents a late transition metal selected from one of the Group 5–12 transition metals, which metal is not in its highest oxidation state.

52. The method of claim 51, wherein the metal atom is selected from the group consisting of Cr, Mn, V, Fe, Mo, W, Ru and Ni.

53. The method of claim 50, wherein the M is Group 6 transition metal.

54. The method of claim 53, wherein the M is Cr(III).

55. The method of claim 50, wherein which are represented by the general formula 104:

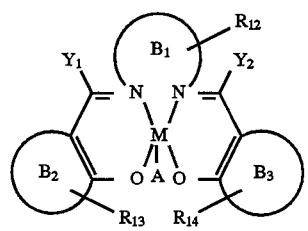

in which the $B_1$ moiety represents a diimine bridging substituent represented by —$R_{15}$—$R_{16}$—$R_{17}$—, wherein $R_{15}$ and $R_{17}$ each independently are absent or represent an alkyl, an alkenyl, or an alkynyl, and $R_{16}$ is absent or represents an amine, an imine, an amide, a phosphoryl, a carbonyl, a silyl, an oxygen, a sulfur, a sufonyl, a seleium, a carbonyl, or an ester;

each of $B_2$ and $B_3$ independently represent rings selected from a group consisting of cycloalkyls, cycloalkenyls, aryls, and heterocyclic rings, which rings comprising from 4 to 8 atoms in a ring structure;

$Y_1$ and $Y_2$ each independently represent hydrogen, halogens, alkyls, alkenyls, alkyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$, $R_{12}$, $R_{13}$, and $R_{14}$ each independently are absent, or represent one or more covalent substitutions of $B_1$, $B_2$ and $B_3$ with halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$, wherein $R_{12}$ can occur on one or more positions of $-R_{15}-R_{16}-R_{17}-$, or any two or more of the $R_{12}$, $R_{13}$, $R_{14}$, $Y_1$ and $Y_2$ taken together form a bridging substituent;

$R_7$ represents an aryl, a cycloalkyl, a cycloalkenyl, a heterocycle, or a polycycle;

m is zero or an integer in the range of 1 to 8;

M represents a transition metal; and

A represents a counterion or a nucleophile, wherein $R_{12}$, $R_{13}$, $R_{14}$, $Y_1$ and $Y_2$ are selected such that the catalyst is asymmetric.

56. The method of claim 50, wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

or any two or more of the substituents $R_{30}$, $R_{31}$, $R_{32}$, and $R_{33}$ taken together form a carbocyle or heterocycle having from 4 to 8 atoms in the ring structure;

$R_7$ represents an aryl, a cycloalkyl, a cycloalkenyl, a heterocycle or a polycycle; and m is zero or an integer in the range of 1 to 8.

57. The method of claim 50, wherein $R_{30}$, $R_{31}$, $R_{32}$, and $R_{33}$ are chosen such that the substrate has a plane of symmetry.

58. The method of claim 50, wherein the cyclic substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

59. The method of claim 50, which process is an enantioselective ring opening.

60. The method of claim 50, which process is a diastereoselective ring opening.

61. The method of claim 60, which diastereoselective ring opening produces a kinetic resolution.

62. A method of stereoselectively opening a ring of a cyclic compound of the general formula:

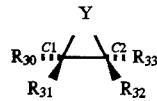

in which

Y represents O, S, $N(R_{50})$, $C(R_{52})(R_{54})$, or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1-C_5$ alkyl, O, S, carbonyl, or $N(R_{50})$; and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y;

which method comprises reacting a nucleophile with said cyclic compound in the presence of at least a catalytic amount of a chira metallosalenate catalyst.

63. The method of claim 62, wherein the metalosalenate catalyst is represented by the general formula:

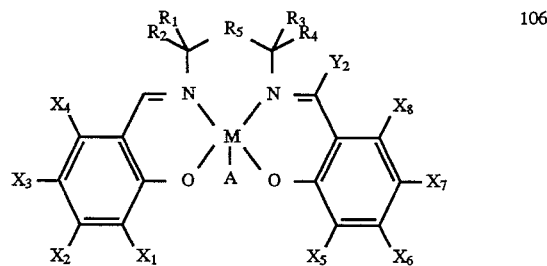

in which each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, akynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

or any two or more of the substituents taken together form a carbocycle or heterocycle having from 4 to 10 atoms in the ring structure;

$R_7$ represents an aryl, a cycloalkyl, a cycloalkenyl, a heterocycle or a polycycle;

m is zero or an integer in the range of 1 to 8;

M represents a transition metal; and

A represents a counterion or a nucleophile;

wherein if $R_5$ is absent, at least one of $R_1$ and $R_2$ is taken together with at least one of $R_3$ and $R_4$ to form a bridging substituent, and each of of the substituents of 106 are selected such that the salenate is asymmetric.

64. The method of claim 62, wherein the substituents wherein the substituents $R_{30}$, $R_{31}$, $R_{32}$, and $R_{33}$ each independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

or any two or more of the substituents $R_{30}$, $R_{31}$, $R_{32}$, and $R_{33}$ taken together form a carbocyle or heterocycle having from 4 to 8 atoms in the ring structure;

$R_7$ represents an aryl, a cycloalkyl, a cycloalkenyl, a heterocycle or a polycycle; and m is zero or an integer in the range of 1 to 8.

65. The method of claim 62, wherein $R_{30}$, $R_{31}$, $R_{32}$, and $R_{33}$ are chosen such that the substrate has a plane of symmetry.

66. The method of claim 62, wherein the substrate is selected from the group consisting of epoxides, aziridines, episulfides, cyclopropanes, cyclic carbonates, cyclic thiocarbonates, cyclic sulfates, cyclic anhydrides, cyclic phosphates, cyclic ureas, cyclic thioureas, lactams, thiolactams, lactones, thiolactones and sultones.

67. The method of claim 63, wherein the M represents a late transition metal from one of the Group 5–12 transition metals.

68. The method of claim 67, wherein the metal atom is selected from the group consisting of Cr, Mn, V, Fe, Mo, W, Ru and Ni.

69. The method of claim 63, wherein the M is Group 6 transition metal.

70. The method of claim 69, wherein the M is Cr(III).

71. The method of claim 62, which process is an enantioselective ring opening.

72. The method of claim 62, which process is a diastereoselective ring opening.

73. The method of claim 72, which diastereoselective ring opening produces a kinetic resolution.

74. A method of resolving enantiomers from a racemic mixture of a chiral cyclic compound having the general form

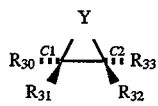

118 in which

Y represents O, S, N($R_{50}$), C($R_{52}$)($R_{54}$), or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or N($R_{50}$); and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y;

the method comprising contacting a mixture of the compound and its enantiomer with a nucleophile able to react with the ring structure in the presence of a chiral catalyst having the form:

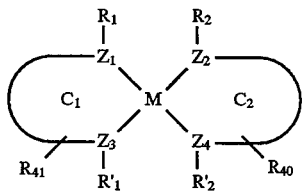

100 in which $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents the late transition metal; and

A represents a counterion or a nucleophile, wherein each $R_1$, $R_2$, $R'_1$, $R'_2$ $R_{40}$ and $R_{41}$ are selected to provide at least one stereogenic center in said tetradentate ligand, under conditions wherein the ring of one enantiomer is selectively opened leaving the other enantiomer substantially unchanged.

75. The method of claim 74, wherein $R_1$, $R_2$, $R'_1$ and $R'_2$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

each $R_{40}$ and $R_{41}$ occuring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or —$(CH_2)_m$—$R_7$;

$R_7$ represents an aryl, a cycloalkyl, a cycloalkenyl, a heterocycle or a polycycle; and m is zero or an integer in the range of 1 to 8.

76. The method of claim 74, wherein each $Z_1$, $Z_2$, $Z_3$ and $Z_4$ are independently selected from the group consisting of nitrogen, oxygen, phosphorus, arsenic, and sulfur.

77. A method of providing a chiral carbonate, comprising reacting a prochiral epoxide with carbon dioxide in the presence of a chiral catalyst and an auxiliary catalyst such that a chiral carbonate is formed, wherein the catalyst chiral catalyst comprises an asymmetric tetradentate ligand complexed with a metal atom, which complex has a rectangular planar or rectangular pyramidal geometry.

78. A method of providing a chiral carbonate, comprising reacting a prochiral epoxide with carbon dioxide in the presence of a chiral catalyst and an auxiliary catalyst such that a chiral carbonate is formed, wherein the catalyst chiral catalyst comprises an asymmetric tridentate ligand complexed with a metal atom, which complex has a planar geometry.

79. A method of stereospecifically expanding a ring of a cyclic compound having the form:

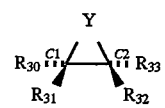

118 in which

Y represents O, S, N($R_{50}$), C($R_{52}$)($R_{54}$), or has the formula A—B—C; wherein $R_{50}$ represents a hydrogen, an alkyl, a carbonyl-substituted alkyl, a carbonyl-substituted aryl, or a sulfonate, $R_{52}$ and $R_{54}$ each independently represent an electron-withdrawing group; A and C are independently absent, or represent a $C_1$–$C_5$ alkyl, O, S, carbonyl, or N($R_{50}$); and B is a carbonyl, a thiocarbonyl, a phosphoryl, or a sulfonyl; and $R_{30}$, $R_{31}$, $R_{32}$, and $R_{33}$ represent organic or inorganic substituent which form a covalent bond with the C1 or C2 carbon atoms of 118, and which permit formation of a stable ring structure including Y;

the method comprising reacting a ring expansion agent with said cyclic compound in the presence of a chiral catalyst having the form

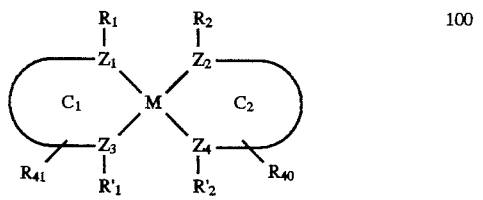

in which $Z_1$, $Z_2$, $Z_3$ and $Z_4$ each represent a Lewis base;

the $C_1$ moiety, taken with $Z_1$, $Z_3$ and M, and the $C_2$ moiety, taken with $Z_2$, $Z_4$ and M, each, independently, form a heterocycle;

$R_1$, $R_2$, $R'_1$ and $R'_2$ each, independently, are absent or represent a covalent substitution with an organic or inorganic substituent permitted by valence requirements of the electron donor atom to which it is attached, $R_{40}$ and $R_{41}$ each independently are absent, or represent one or more covalent substitutions of $C_1$ and $C_2$ with an organic or inorganic substituent permitted by valence requirements of the ring atom to which it is attached, or any two or more of the $R_1$, $R_2$, $R'_1$, $R'_2$ $R_{40}$ and $R_{41}$ taken together form a bridging substituent;

with the proviso that $C_1$ is substituted at at least one site by $R_1$, $R'_1$ or $R_{41}$, and $C_2$ is substituted at at least one site by $R_2$, $R'_2$ or $R_{40}$, and at least one of $R_1$, $R'_1$ and $R_{41}$ is taken together with at least one of $R_2$, $R'_2$ and $R_{40}$ to form a bridging substituent so as to provide $Z_1$, $Z_2$, $Z_3$ and $Z_4$ as a tetradentate;

M represents the late transition metal; and

A represents a counterion or a nucleophile, wherein each $R_1$, $R_2$, $R'_1$, $R'_2$ $R_{40}$ and $R_{41}$ are selected to provide at least one stereogenic center in said tetradentate ligand, under conditions wherein the ring of one enantiomer is selectively opened leaving the other enantiomer substantially unchanged, under conditions such that said ring of said cyclic compound is stereoselectively expanded.

80. The method of claim 78, wherein $R_1$, $R_2$, $R'_1$ and $R'_2$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

each $R_{40}$ and $R_{41}$ occuring in 100 independently represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

$R_7$ represents an aryl, a cycloalkyl, a cycloalkenyl, a heterocycle or a polycycle; and m is zero or an integer in the range of 1 to 8.

81. The method of claim 78, wherein each $Z_1$, $Z_2$, $Z_3$ and $Z_4$ are independently selected from the group consisting of nitrogen, oxygen, phosphorus, arsenic, and sulfur.

82. A composition comprising an aged metallosalenate catalyst, which catalyst is represented by the general formula:

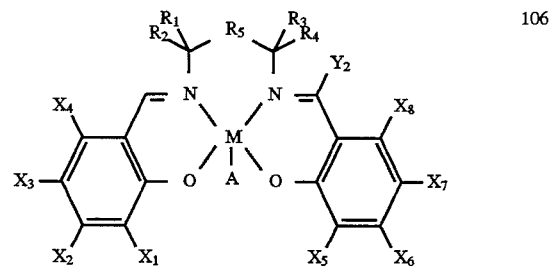

in which each of the substituents $R_1$, $R_2$, $R_3$, $R_4$, $R_5$, $Y_1$, $Y_2$, $X_1$, $X_2$, $X_3$, $X_4$, $X_5$, $X_6$, $X_7$, and $X_8$, independently, represent hydrogen, halogens, alkyls, alkenyls, alkynyls, hydroxyl, amino, nitro, thiol, amines, imines, amides, phosphoryls, phosphonates, phosphines, carbonyls, carboxyls, silyls, ethers, thioethers, sulfonyls, selenoethers, ketones, aldehydes, esters, or $-(CH_2)_m-R_7$;

or any two or more of the substituents taken together form a carbocycle or heterocycle having from 4 to 10 atoms in the ring structure;

$R_7$ represents an aryl, a cycloalkyl, a cycloalkenyl, a heterocycle or a polycycle;

m is zero or an integer in the range of 1 to 8;

M represents a transition metal; and

A represents a nucleophile;

wherein if $R_5$ is absent, at least one of $R_1$ and $R_2$ is taken together with at least one of $R_3$ and $R_4$ to form a bridging substituent, and each of of the substituents of 106 are selected such that the salenate is asymmetric.

* * * * *

UNITED STATES PATENT AND TRADEMARK OFFICE
CERTIFICATE OF CORRECTION

PATENT NO. : 5,665,890
DATED : September 9, 1997
INVENTOR(S) : Eric N. Jacobsen, James L. Leighton, Luis E. Martinez It is certified that error appears in the above-identified patent and that said Letters Patent is hereby corrected as shown below:

At column 1, line 5: insert

-- GOVERNMENT SUPPORT

This invention was made with Government support under Grant No. GM43214, awarded by the National Institutes of Health. The Government has certain rights to the invention.--

Signed and Sealed this

Eighth Day of September, 1998

Attest:

BRUCE LEHMAN

Attesting Officer

Commissioner of Patents and Trademarks